United States Patent [19]

Leenhouts et al.

[11] Patent Number: 5,627,072
[45] Date of Patent: May 6, 1997

[54] FOOD-GRADE VECTOR SUITABLE FOR TRANSFORMING A FOOD-GRADE HOST CELL USE OF SAID VECTOR FOR TRANSFORMING FOOD-GRADE HOST CELLS AND USE OF SAID TRANSFORMED CELLS IN BIOTRANSFORMATION PROCESSES

[75] Inventors: Cornelis J. Leenhouts, Haren; John D. Marugg, Utrecht; Cornelis T. Verrips, Maassluis, all of Netherlands

[73] Assignee: Van Den Bergh Foods Co., Division of Conopco Inc., Lisle, Ill.

[21] Appl. No.: 368,397

[22] Filed: Jan. 3, 1995

Related U.S. Application Data

[63] Continuation of Ser. No. 32,739, Mar. 16, 1993, abandoned, which is a continuation of Ser. No. 795,412, Nov. 20, 1991, abandoned.

[30] Foreign Application Priority Data

Nov. 23, 1990 [EP] European Pat. Off. ............ 90203114

[51] Int. Cl.$^6$ ............................ C12N 15/00; C12N 1/20; C12P 21/06; A23L 1/00
[52] U.S. Cl. .................................. 435/320.1; 435/252.9; 435/69.1; 435/172.3; 426/52
[58] Field of Search ............................ 435/320.1, 252.9, 435/69.1, 172.3; 426/52

[56] References Cited

U.S. PATENT DOCUMENTS

| | | | |
|---|---|---|---|
| 4,977,088 | 12/1990 | von Wright et al. | 435/252.3 |
| 5,061,625 | 10/1991 | Mattes et al. | 435/172.3 |
| 5,459,072 | 10/1995 | McKay et al. | 435/320.1 |

FOREIGN PATENT DOCUMENTS

| | | | |
|---|---|---|---|
| 1264685 | 1/1990 | Canada | C12N 1/20 |
| 0255153 | 9/1985 | European Pat. Off. | |
| 0355036 | 2/1990 | European Pat. Off. | C12N 15/00 |
| WO85/03945 | 9/1985 | WIPO | C12N 15/00 |
| 8503945 | 2/1988 | WIPO | |
| 8901970 | 3/1989 | WIPO | |
| WO89/01970 | 3/1989 | WIPO | C12N 15/00 |

OTHER PUBLICATIONS von Wright et al., "Isolation of a Replication Region of a large Lactococcal Plasmid and Use in Cloning of a Nisin Resistance Determinant,"0 Applied and Environmental Microbiology 56(7):2029–2035. (Jun. 1990).

Leenhouts et al., "Campbell–Like Integration of Heterologous Plasmid DNA into the chromosome of *Lactococcus lactis* subsp. lactis," Applied and Environmental Microbiology 55(2):394–400. (Feb. 1989).

Chopin et al., "Insertion and Amplification of Foreign Genes in the *Lactococcus lactis* subsp. lactic Chromosome," Applied and Environmental Microbiology 55(7):1769–1774. (Jul. 1989).

LaFauci, G. et al., Mapping of rRNA genes with integrable plasmids in Bacillus subtilis, J. Bacteriol. 165:204–214 Jan. 1986.

Hayes, F. et al. pAMB1–associated mobilization of proteinase plasmids from Lactococcus lactis subsp. lactis UC317 and L. lactis subsp. cremoris UC205, Applied and Environment. Microbiol. 56: 195–201 Jan. 1990.

Vos, P. et al, A maturation protein is essential for production of active forms of Lactococcus lactus SK11 serine proteinase located in or secreted from the cell envelope, J. Bacteriol. 171: 2795–2802 May 1989.

Haandrikman et al., "Identification of a Gene Required for Maturation of an Extracellular Lactococcal Serine Proteinase" v. 171 No. 5 J. Bacteriol. (1989) pp. 2789–2794.

"Evidence for Plasmid Linkage of Raffinose Utilization and Associated alpha–Galactosidase and Sucrose Hydrolase Activity in Pediococcus pentasaceus", v 51, No. 1 App. Envir. Microb. pp. 105–109 (1986) Gonzales et al.

Overbeeke et al. Chemical Abstracts vol.113 No. 5, p. 461, Abstract No. 38839V (1990).

von Wright et al. Applied and Environmental Microbiology, vol. 56, No. 7, pp. 2029–2035 (Jul., 1990).

Leenhouts et al, Applied and Environmental Microbiology, vol. 55, No. 2, pp. 394–400 (Feb. 1989).

Chopin et al, Applied and Environmental Microbiology, vol. 55, No. 7, pp. 1769–1774 (Jul., 1989).

Haandrikman et al, Journal of Bacteriology, vol. 171, No. 5, pp. 2789–2794 (May, 1989).

Gonzalez et al, Applied and Environmental Microbiology, vol. 51, No. 1, pp. 105–109 (Jan. 1986).

Chemical Abstracts, vol. 113, No. 5, p. 461, Abstract No. 38839v.

*Primary Examiner*—Mindy Fleisher
*Assistant Examiner*—Bonnie D. Weiss
*Attorney, Agent, or Firm*—Cushman Darby & Cushman IP Group Pillsbury Madison & Sutro LLP

[57] ABSTRACT

A food-grade vector is provided which is suitable for transforming a food-grade host cell and is incapable of replicating autonomously in the host cell due to deletion of the replicase gene.

30 Claims, 18 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 10 nucleotides
( B ) TYPE: nucleotide
( C ) STRANDEDNESS: single
( D ) TOPOLOGY: linear ( x i ) SEQUENCE DESCRIPTION: SEQ ID NO:1:

AAAGATCTTT                                                                                                                 10

FOOD-GRADE VECTOR SUITABLE FOR TRANSFORMING A FOOD-GRADE HOST CELL USE OF SAID VECTOR FOR TRANSFORMING FOOD-GRADE HOST CELLS AND USE OF SAID TRANSFORMED CELLS IN BIOTRANSFORMATION PROCESSES

This is a continuation of application Ser. No. 08/032,739, filed on Mar. 16, 1993, abandoned, which is a continuation of Ser. No. 07/795,412, filed Nov. 20, 1991, now abandoned.

Lactic acid bacteria play a very important role in a large number of food fermentation processes. The fermentation processes in which lactic acid bacteria play an important role do not only include fermentation of milk, resulting in products like yoghurt, sour cream and cheese, but also of meat, fish, fruit, vegetables, beans and cereal products (see for instance Biotechnology Volume V, Editors H.-J. Rehm and G. Reed, Verlag Chemic, 1983).

The role of lactic acid bacteria is to make these fermented products microbiologically more stable and to improve the taste and palatability of these products. More recent studies have shown that fermented food products containing certain types of lactic acid bacteria are also important in the development of new products that have a positive impact on the health of the consumers (see for recent review: FEMS Microb. Rev. 87, 175–188). Consequently lactic acid bacteria are of large economic importance. In a large number of studies (Chopin, M. C., A. Moillo-Batt, and A. Rouault, 1985. FEMS Microbiol. Lett. 26:243–245; Davies, F. L. H. M. Underwood, and M. J. Gasson, 1981. J. Appl. Bacteriol 51:325–337; Gasson, M. J., 1983. J. Bacteriol. 154:1–9) it has been found that genetic properties, that are important to ensure that lactic acid bacteria perform the right type of fermentation, are located on extrachromosomal DNA, most often called plasmids. Plasmids have the advantage that they exist normally in the cell in multimeric form, which also means that a certain gene located on such a plasmid exists in the cell in multicopy form, which may result in a higher expression of the proteins encoded by these genes.

However the disadvantage of plasmids is that they are unstable, resulting in a possible loss of the plasmids from the cells at a certain stage. It has been found for example that after ripening in cheeses like Cheddar and Gouda a considerable part of the cells that were originally capable of producing proteinase (prt$^+$) have lost the plasmid encoding said proteinase, that is indispensible for achieving the desired ripening of cheese (McKay 1983, Ant. v. Leeuwenhoek 49, 259–274).

Plasmids also play an important role in recombinant DNA technology, a technology in which homologous or heterologous genetic information can be introduced into host cells. In such processes plasmids serve as vector on which the new genetic property can be integrated and subsequently transferred into the host cell (WO 85/03945). To be able to detect whether such a transfer has been successful and to maintain the plasmid in the transformed cell, the plasmids must also contain a so-called selection marker, which is usually a gene that confers resistance to an antibiotic or another agent that may kill cells that do not contain said plasmid (Chopin, M. C. A. Chopin, A. Rouault, and N. Gallcron. 1989. Appl. Environ. Microbiol. 55:1769–1774; De Vos, W. M., and G. Simons. 1988. Biochimie 70:461–473).

The disadvantage of plasmids containing such selection markers for use in food fermentation lies in the high costs of the antibiotics and the fact that they have to be present in the medium in which the bacteria have to be cultivated. This has consequently led to the development of so-called food-grade vectors on which the selection markers are often an auxotrophic marker (EP-A-0,355,036). In this procedure host cells are the so-called auxotrophic mutants which, in contrast to the so-called prototrophic wild type strains, are incapable of optimum growth in media without supplementation of nutrient(s). Lactic acid bacteria are quite fastidious and often wild types need the presence of amino acids or vitamins in the medium. Transfer of a vector containing a gene(s) which is (are) absent or deficient in the host cell, and subsequent growth in a medium which does not contain the additional nutrient(s) can serve as a method for successful transformation of the host cell and maintenance of the vector in the transformed host cell. The disadvantage of this approach is that host strains have to be used that either lack the gene encoding said marker on their chromosome or contain a non functional gene, and that such host strains often first have to undergo a mutation to inactivate or eliminate said gene, before the plasmid can be transferred to the cell and can serve as a marker. The mutation methods which are used to mutate a prototrophic strain so that it becomes an auxotrophic strain have the disadvantage that they nearly always damage other properties as well.

EP-A-0,355,036 describes a procedure in which a lactic acid bacterium, which completely lacks one or two indispensible enzymes for lactose fermentation or lacks sufficient activity of said enzyme(s), is transformed with a DNA fragment containing a marker in the form of code(s) for the missing indispensible enzyme(s) for lactose fermentation. EP-A-0,355,036 therefore describes a procedure, wherein the plasmid is equipped with a property that is new for the cell into which it is transferred and gives the cell a real advantage during food fermentation. EP-A-0,355,036 not only describes the use of a DNA fragment that contains a functional replicon but also the use of a DNA fragment without a functional replicon. The latter DNA fragment also contains a DNA sequence which is homologous with a stretch of the DNA of the lactic acid bacterium used, as a result of which the entire DNA fragment or essential parts thereof is or are integrated into the DNA of said lactic acid bacterium. In EP-A-0,355,036 the two central components are firstly the lactose-deficient lactic acid bacterium and secondly the DNA coding for at least one or more enzymes of the lactose metabolism.

A major disadvantage of the approach described in EP-A-0,355,036 lies in the facts that lactose is only present in reasonable quantities in milk and that the marker will only function in a medium containing lactose. There is however a great abundance of food products that contain other sugars such as sucrose, raffinose, stachyose and verbascose, which sugars comprise a sucrose (glucose-fructose) to which an increasing number of D-galactose residues are coupled. Raffinose occurs in cereal grains, soybean and many legumes. Stachyose occurs in many genera of *leguminosae* and *labiateae*, the seeds of glycine max and the rhizomes of *Stachys sieboldii* and nervacose is present in soybeans, seeds of lucerne and meadow sage and rhizomes of Teucnium. Whereas sucrose is a very suitable carbon source for many lactic acid bacteria (Bergey's Manual), only a small number of said bacteria have the ability to grow on raffinose, stachyose or verbascose. Furthermore other bacteria are not well equipped to ferment these sugars and therefore said sugars are hardly degraded in the upper part of the G.I. tract of humans. Consequently products containing reasonable amounts of said sugars often cause discomfort to the consumer in the form of flatulence.

The subject invention concerns a food-grade vector suitable for transforming a food-grade host cell and incapable of replicating autonomously in said host cell, said vector comprising:

1) at least one stretch of nucleotides capable of hybridizing with chromosomal DNA of the non-transformed host cell enabling said vector to integrate stably into the chromosome of said host cell after transformation and
2) at least one stretch of foreign DNA selected from:
   a) stretches comprising at least one DNA sequence that codes for at least one product enabling the transformed host cell to metabolize a substrate that cannot be metabolized by the non-transformed host cell, wherein at least said DNA sequence and the product encoded by said DNA sequence are foreign for a prototrophic strain of said non-transformed host cell
   b) stretches comprising at least one DNA sequence that codes for at least one product enabling the transformed host cell to grow in the presence of a food grade, natural bacteriocidal agent, wherein at least said DNA sequence and the product encoded by said sequence are foreign for the non-transformed host cell.

Food-grade vectors according to the invention only contain sequences of DNA that originate from a food-grade source. Preferably the vectors according to the invention contain DNA obtained from a food grade organism.

In one embodiment of the food-grade vector according to the invention the food-grade vector contains at least one stretch of foreign DNA comprising at least a DNA sequence that codes for at least one product enabling the transformed host cell to metabolize a substrate that cannot be metabolized by the non transformed host cell. Such a food-grade vector according to the invention can contain DNA coding for a number of various products enabling the transformed host cell to metabolize a number of different substrates that the non transformed host cell cannot metabolize. Said products can be encoded on different stretches of foreign DNA and/or on one stretch of foreign DNA comprising more than one DNA sequence.

In another embodiment the food-grade vector according to the invention can contain DNA that codes for at least one product enabling the transformed host cell to grow in the presence of food-grade natural bacteriocidal agent, wherein at least said DNA sequence and the product encoded by said sequence are foreign for the non transformed host cell. Such a food-grade vector according to the invention can contain DNA coding for a number of various products enabling the transformed host cell to grow in the presence of a food-grade natural bacteriocidal agent, wherein said DNA sequences and the products encoded by said sequences are foreign for the non transformed host cell. Said products can be encoded on different stretches of foreign DNA and/or on one stretch of foreign DNA comprising more than one DNA sequence.

The food-grade vector accoding to the invention can also comprise one or more of the stretches of foreign DNA described under a) as well as one or more stretches of foreign DNA as described under b).

Preferred food-grade host cells are bacteria that produce lactic acid. Most lactic acid bacteria can only use glucose and lactose as substrate and cannot for example use stachyose and raffinose as substrate.

Preferably the food-grade vector according to the invention shall comprise a stretch of foreign DNA comprising a DNA sequence that codes for a food-grade selectable marker. For example such a stretch of foreign DNA can comprise a DNA sequence at least encoding an enzyme that is essential for metabolizing a polysaccharide.

Another suitable food-grade vector according to the invention comprises a stretch of foreign DNA comprising a DNA sequence that codes for a proteinase. Preferably such a food-grade vector also comprises a DNA sequence that codes for a maturase, as a maturase is often required for a functional proteinase. DNA sequences coding for proteinase and maturase derivable from *Lactococcus lactis* are particularly suited for use in food-grade vectors according to the invention.

The term "derivable from" in this instance includes any DNA sequence coding for a functional product corresponding to the proteinase actually present in *Lactococcus lactis*. This term therefore includes any DNA sequences coding for a functional proteinase having mutations, deletions etc. in comparison to the DNA sequence coding for proteinase that can actually be derived from *Lactococcus lactis*.

The stretch of foreign DNA can also comprise a DNA sequence encoding a precursor of an enzyme as described above. The stretch of foreign DNA can also be composed of a combination of a DNA sequence encoding the enzyme and a presequence that is derived from the host cell.

In the case of such a lactic acid bacterium that can only use glucose or sucrose or lactose for example, the stretch of foreign DNA can comprise a DNA sequence that codes for an enzyme that is essential for metabolizing a polysaccharide other than these sugars. The foreign DNA sequence in the food-grade vector according to the invention can for example be DNA encoding at least an α-galactosidase. This foreign DNA can function as selection marker if the food-grade vector according to the invention is transformed to a host cell which before transformation could not for example metabolize raffinose or stachyose. The presence of α-galactosidase in the transformed host cell due to expression of the foreign DNA coding for α-galactosidase leads to the splitting off of galactose from a large number of sugars for example raffinose, stachyose but also guar gum, thereby giving rise to metabolizable products and subsequently to growth of the transformed host cell on media containing such carbohydrates that were previously non-metabolizable.

Lactic acid bacteria containing such a food-grade vector, comprising DNA coding for α-galactosidase, are therefore provided with the advantage of faster growth, on a larger number of foods and to a much higher biomass. The presence of such foreign DNA in the transformed host cell eliminates the necessity of a vector containing an antibiotic resistance or an auxotrophic marker gene to maintain the presence of the vector in the transformed host cell.

A key element in the present invention is therefore that α-galactosidase or another polysaccharide splitting enzyme such as inulinase and/or sucrose hydrolase are excellent selection markers to use in the food-grade vectors according to the invention.

There are a number of good natural sources of α-galactosidase available, and the characteristics of the α-galactosidase vary according to the source from which it is derived, consequently food-grade vectors according to the invention can contain foreign DNA encoding α-galactosidase from various sources, depending on the desired characteristics of the enzyme. The isolation, characterisation and molecular cloning of the α-galactosidase gene from *Cyamopsis tetragonoloba* into several host cells has been described (Overbeeke et al., 1984, Plant Mol. Biol. 13:541–550). This α-galactosidase for example is very suitable to hydrolyse galactose side chains under conditions of low free water, and therefore host cells, such as lactic acid bacteria, that contain a food-grade vector according to the invention comprising such DNA that codes for a precursor form of said enzyme are very suitable for use in solid state fermentations (Critchley, 1987. In Biocatalysis in organic media, pg 173–183, Elsevier). For semi-solid or liquid fermentations other genes coding for other α-galactosidases can be used (Dey and Pridham 1972, Adv. Enzym Rel. Annot. Mol. Biol. 36:91–120). The α-galactosidase that has been isolated from *Verbascum thapsus* has been found to possess superior properties for application in semi-solid or liquid fermentations. Therefore a preferred embodiment of the invention relates to a food-grade vector that contains the gene coding for α-galactosidase, as can be obtained from *Verbascum thapsus*. Other preferred embodiments of the food-grade vectors according to the invention are food-grade vectors containing the α-galactosidase gene derived from guar gum or the yeast *Saccharomyces carlsbergensis* or the plant *Cyamopsis tetragonoloba*. Still another preferred embodiment of the food-grade vectors according to the invention are food-grade vectors containing the α-galactosidase gene derived from the lactic acid bacterium *Pediococcus pentosaceus*, as described by Gonzales G. F. and Kunka B. S. (Appl. Env. Microbiol. 51 (1986) 105–109), or the combined DNA coding for α-galactosidase, and sucrose hydrolase of this strain.

However the present invention is not limited to the presence of foreign DNA encoding α-galactosidase, as selection marker and growth promoter in the food-grade vector. Another example of foreign DNA that can be a component in the food-grade vector according to the invention is DNA coding for at least the precursor of inulinase. The presence of this DNA on the food-grade vector will enable host cells into which the food-grade vector according to the invention is transferred to grow on foods containing poly-fructans, such as foods derived from crops like Jerusalem artichokes.

Inulinases are also widespread in nature. For food fermentation processes the inulinase of *Aspergillus niger* is very suitable for use in solid or semi-solid fermentations, whereas the inulinase from *Kluyveromyces marxianus* is very suitable for application in semi-solid and liquid food fermentations. Therefore preferred embodiments of the invention relate to a food-grade vector according to the invention containing DNA coding for inulinase that can be obtained from *Aspergillus niger* or from *Kluyveromyces marxianus*.

Another suitable food-grade vector according to the invention contains DNA coding for a sucrose hydrolase. In particular DNA coding for a sucrose hydrolase derivable from the lactic acid bacterium *Pediococcus pentosaceus*.

The food-grade vector according to the invention can contain DNA coding for a bacteriocidal agent and/or immune proteins for such a bacteriocidal agent and/or proteins involved in the proper secretion of such a bacteriocidal agent.

The food-grade vector according to the invention can also contain a presequence before the foreign DNA sequence, which presequence is derived from the host cell so that the food-grade vector encodes a precursor enzyme containing a signal enzyme of the host cell.

The food-grade vectors according to the invention must also contain a certain stretch of nucleotides homologous to that of chromosomal DNA of the host cell and they must be unable to maintain themselves in the host cell, leading to stable integration of the whole food-grade vector or of essential parts of said vector. Preferably the food-grade vectors should integrate in a multimeric form into the chromosome of the host cell. This can be achieved by using a food-grade vector according to the invention that contains a stretch of nucleotides that is present in more than one copy in the host cell to enable integration in the host cell. DNA sequences derived from DNA of the host cell encoding 5S or 16S or 23S RNA can be present in the vector according to the invention as the homologous DNA of the host cell enabling integration.

The stretch of nucleotides enabling integration is preferably derivable from DNA that comprises at least part of a non-essential portion of the chromosome of the non-transformed host cell. (In this instance the term "derivable from" implies that the stretch of nucleotides in the vector according to the invention must show enough homology with the chromosomal DNA to enable sufficient hybridisation for an integration event to occur.). The integration of the vector will subsequently take place in said non-essential portion of the chromosome of the host cell and not lead to the loss of an essential function of the host cell.

It is preferable for the integration to take place in a non-essential selectable gene of the chromosome of the non-transformed host cell. This can be a selection criterion for transformed host cells. A suitable example of a selectable gene is the XPDAP (X prolyldiaminopeptidase) gene. In a plate assay (as described by Miller et al J. Bacteriol. 127 (1976) 440–497) an XPDAP⁺ strain will give a red colony and an XPDAP⁻ strain will give a white colony.

In order to integrate only a part of the vector according to the invention, it is possible to use a vector in which the DNA to be integrated is situated between two non-identical stretches of nucleotides that enable integration. Preferably the two non-identical stretches of nucleotides enabling the integration comprise at least part of the same gene. The distance between the stretches of nucleotides must be small enough to allow double cross-over.

Host cells into which the food-grade vector according to the invention have been transferred have the same advantages as those host cells that have been obtained after having been transformed with plasmids, namely the presence in the host cells of a number of copies of the gene of interest. However the host cells obtained that contain the food-grade vector according to the invention do not have the disadvantages of instability or the ensurance of said stability with unnatural substances.

The food-grade vector according to the invention may not only contain a DNA sequence originating from the selected host and foreign DNA enabling the transformed host cell to metabolize a substrate that cannot be metabolized by the non transformed host cell and/or foreign DNA that codes for at least one product enabling the transformed host cell to grow in the presence of food-grade natural bacteriocidal agent in contrast to the non transformed host cell, but may also contain any other DNA sequence that can be involved in the further upgrading of food that is to be fermented. Said further DNA sequence can code for a product that is foreign for the non transformed host cell, originate from a food-grade organism and be unable to hybridize efficiently with DNA of the non-transformed host cell. An example is a food-grade vector according to the invention, containing one or more DNA sequences coding for enzymes involved in the biosynthesis of essential amino acids. This can be of particular importance for example if the medium that is used in the fermentation is poor in such amino acids, for example cassave.

Another example of such a food-grade vector according to the invention, that contains another DNA sequence involved in the upgrading of food that is to be fermented, contains one or more DNA sequences coding for a proteolytic enzyme such as a proteinase or a peptidase or coding for enzymes involved in the biosynthesis of important taste, flavour or colour compounds. In the case of food-grade vectors containing at least one stretch of foreign DNA selected from category a) i.e. comprising DNA coding for at least one product enabling the transformed host cell to metabolize a substrate that cannot be metabolized by the non transformed host cell, such a stretch of foreign DNA can also comprise one or more DNA sequences coding for the bacteriocidal agents and/or the immuneproteins of these bacteriocidal agents and/or the proteins involved in proper secretion of these bacteriocidal agents. In such a case the latter sort of foreign DNA is not the DNA that provides the selectable marker. In said instance the selectable marker is provided by the foreign DNA enabling the transformed host cell to metabolize a substrate the non transformed cell cannot metabolize. Host cells containing a food-grade vector according to the invention that are selected from the latter group will produce fermented foods that will be more stable against microbial spoilage.

The subject invention also relates to a process for obtaining a transformed food-grade host cell, in such a manner as to enable the host cell to metabolize a substrate that cannot be metabolized by the non-transformed host cell, wherein said food-grade vector is used for transforming the host cell and subsequently stably integrating foreign DNA in the chromosomal DNA of said transformed host cell, said foreign DNA coding for at least one product enabling the transformed host cell to metabolize a substrate that cannot be metabolized by the non-transformed host cell. The subject invention also relates to a process for obtaining a transformed food-grade host cell in such a manner as to enable the host cell to grow in the presence of a food-grade natural bacteriocidal agent in contrast to the non transformed host cell, wherein said food-grade vector is used for transforming the host cell and subsequently stably integrating foreign DNA in the chromosomal DNA of said transformed host cell, said foreign DNA coding for at least one product enabling the transformed host cell to grow in the presence of a food-grade natural bacteriocidal agent in contrast to the non transformed host cell. The subject invention is also directed at a combination of the two abovementioned processes in one process in which a food-grade vector is used enabling the transformed host cell to metabolize a substrate the non transformed cell cannot metabolize and enabling the transformed host cell to grow in the presence of a food-grade natural bacteriocidal agent in contrast to the non transformed host cell.

The subject invention also includes such a process for obtaining a transformed food-grade host cell wherein a vector such as described above is co-transformed with a selectable plasmid, said plasmid subsequently being lost from the transformed host cell after removal of the selective pressure used for maintaining said plasmid in the transformed host cell. It is possible for example to use a plasmid containing an antibiotic resistance gene for the co-transformation and to transform the host cell in the presence of said antibiotic. The principle of using a co-transformation vector for improving the election of transformed host cells is well known. After transformation the host cells can be grown in or on medium without said antibiotic which will result in loss of the plasmid containing the antibiotic resistance marker after a few generations, leading to a food-grade transformed host cell containing the stably integrated foreign DNA coding for at least one product enabling the transformed host cell to metabolize a substrate that cannot be metabolized by the non-transformed host cell and/or containing foreign DNA enabling the transformed host cell to grow in the presence of a food-grade natural bacteriocidal agent in contrast to the non transformed host cell. The selection of such a transformed host cell can be carried out due to the ability of the transformed host cell to metabolize a substrate that the non-transformed host cell cannot metabolize and/or the ability of the transformed cell to grow in the presence of a food-grade natural bacteriocidal agent in contrast to the non transformed host cell. Selection is also possible due to the elimination of activity of a particular gene of the transformed host cell in comparison to the non-transformed host cell, through integration of the vector in said particular gene of the host cell. This can be carried out by using a vector comprising a stretch of nucleotides capable of hybridizing with chromosomal DNA of the host cell comprising a part of said particular gene of the host cell.

The invention also relates to any host cell which is obtained by use of a vector as described above or obtained by the process as described above and also relates to any host cell that contains a vector, such as has been described above, that is stably integrated into the chromosome of the host hell. Preferred host cells are lactic acid bacteria, with most preference for a host cell selected from the genera Bifidobacterium, Enterococcus, Lactobacillus, Lactococcus, Leuconostoc, Pediococcus and Streptococcus or from food-grade strains of the genera Propionibacterium and Staphylococcus.

Furthermore the invention relates to a biotransformation process, wherein either the intact host cells containing the food-grade vector according to the invention or their homogenates or purified forms thereof are used, for example a food fermentation process. The invention relates to any fermentation process, wherein a food-grade substrate and a host cell containing a food-grade vector according to the invention is used.

The biotransformation process according to the invention is preferably related to the use of a food-grade vector containing DNA that at least codes for an enzyme that can split polysaccharides that are not or are poorly metabolized by the large majority of lactic acid bacteria commonly used in food fermentations. Such a fermentation process can also involve the use of another food-grade microorganism.

Increasing the number of varieties of lactic acid bacteria that can ferment sugars like raffinose, stachyose or verbascose is an important feature of this invention, as in that way a wider range of food products can be fermented with lactic acid bacteria. Furthermore lactic acid bacteria that possess the property to ferment these sugars are better equipped to maintain themselves in the G.I. tract, thereby replacing other bacteria that are often pathogenic or may convert food compounds into carcinogens. Therefore these modified lactic acid bacteria according to the invention are very suitable to develop a new range of healthy foods.

Finally the invention also relates to any food product obtained using a biotransformation process as has been described in the specification.

Experimental

All DNA manipulations were performed essentially as described by Maniatis et al. (Molecular Cloning. A Laboratory Manual. Cold Spring Harbor 1982), or as described by the suppliers of restriction enzymes or other DNA-modifying enzymes. Specific techniques for *L. lactis*, and *B. subtilis*, such as media and growth conditions, plasmid isolation, protoplast transformation, electroporation transformation procedures, have been described previously (Leenhouts, K., Kok J., and Venema, G., 1989. Appl. Environ. Microbiol. 55:394–400; Leenhouts, K., Kok J., and Venema, G., 1990. Appl. Environ. Microbiol. 56:2726–2735).

The invention shall be illustrated further in the following examples:

EXAMPLES

Example 1

Construction of plasmids containing only α-galactosidase as marker and expression in *Lactococcus lactis*. The *C. tetragonoloba* α-galactosidase gene was used.

Figure 1:
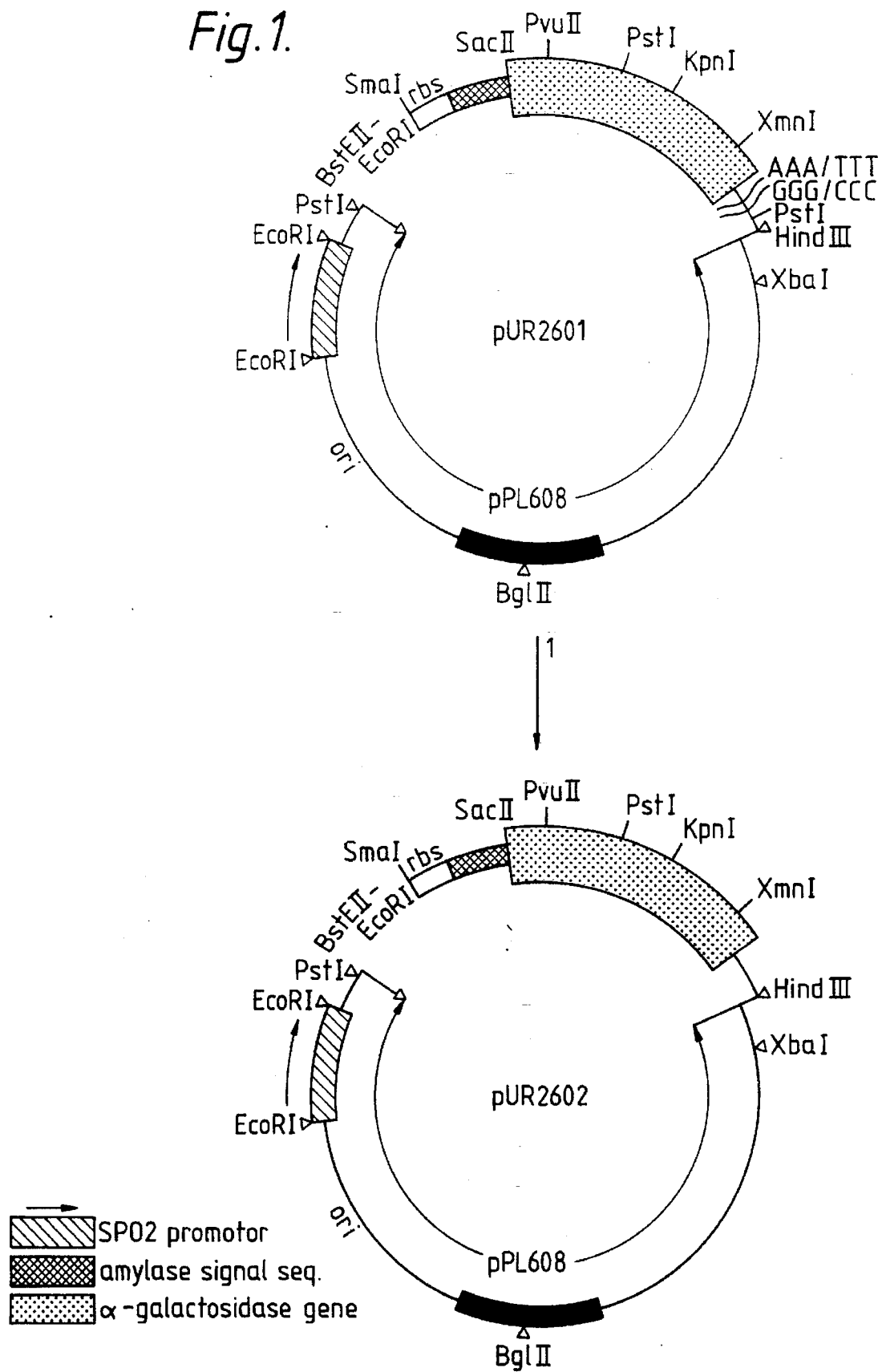
FIG. 1 is a schematic representation of plasmids pUR2601 and pUR2602.
Figure 2:
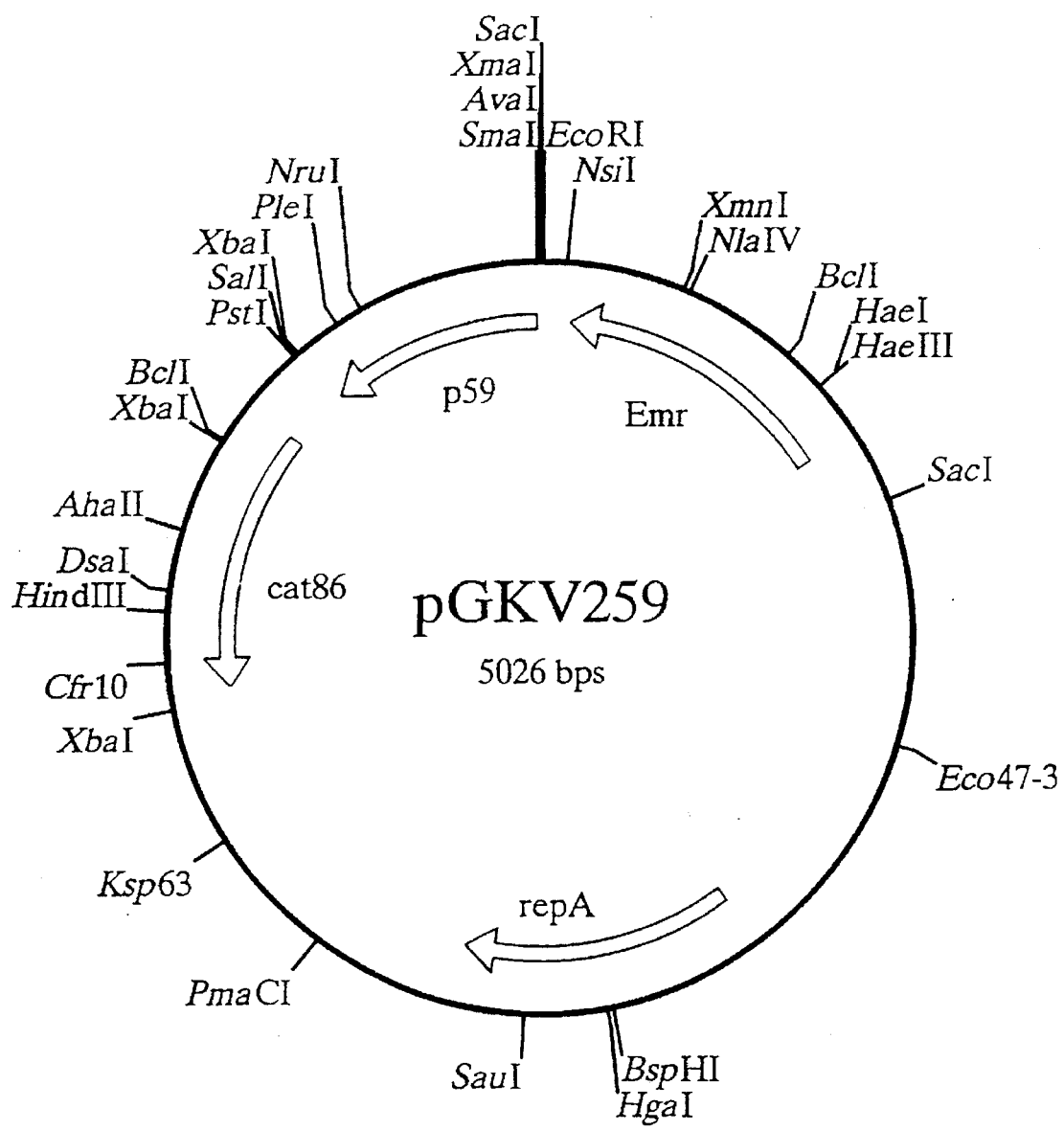
FIG. 2 is a schematic representation of plasmid pGKV259.
Figure 3:
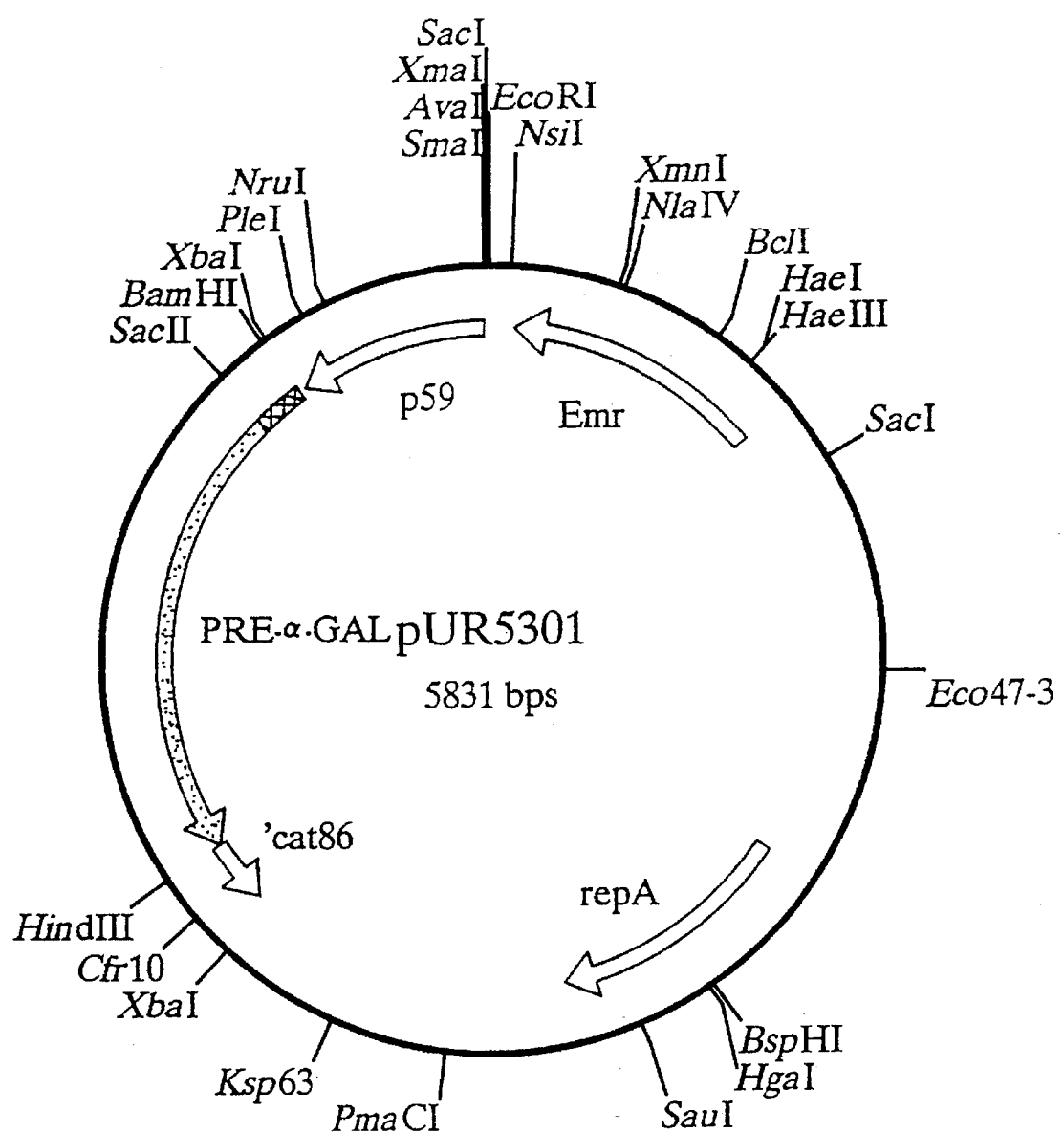
FIG. 3 is a schematic representation of plasmid pUR5301.

Plasmid pUR2601 (FIG. 1) containing the *C. tetragonoloba* mature α-galactosidase gene preceded by the α-amylase signal sequence from *B. amyloliquefaciens* has been described (Overbeeke N., Termorshuizen, G. H. M., Guiseppin, M. L. F. Underwood, D. R., and Verrips, C. T. 1990. Appl. Environ. Microbiol. 56:1429–1434, 1990). In order to remove the A/T and G/C tails in this construct present just downstream of the α-galactosidase gene, the 0.4 kb XmnI-HindIII fragment was replaced by a corresponding, synthetic XmnI-HindIII fragment in which the HindIII-site was positioned immediately downstream of the C-terminal end of the α-galactosidase gene. From the resulting plasmid, called pUR2602 (FIG. 1), the SmaI-HindIII fragment containing the complete pre α-galactosidase gene was isolated and cloned in plasmid pGKV259 (FIG. 2) (van der Vossen, J. M. B. M., van der Lelie, D, and Venema, G, 1987. Appl. Environ. Microbiol. 53:2452–2457), that was first cut with SalI, then treated with Klenow enzyme to blunt the protruding ends, and finally cut with HindIII. This resulted in plasmid pUR5301 (FIG. 3), in which the α-galactosidase gene is under the control of the lactococcal promoter P59 (van der Vossen, J. M. B. M., van der Lelie, D, and Venema, G, 1987. Appl. Environ. Microbiol. 53:2452–2457). When *L. lactis* MG1363 cells were grown, after transformation with pUR5301, on plates containing the indicator X-α-Gal (Overbeeke., N., Termorshuizen, G. H. M., Guiseppin, M. L. F., Underwood, D.R., and Verrips, C. T. 1990. Appl. Environ. Microbiol. 56:1429–1434, 1990) colonies turned blue, indicating that active α-galactosidase was produced. The following steps can be performed in order to obtain plasmid food-grade vectors containing only DNA sequences derived from food-grade organisms, such as *Lactococcus spp.*, or *C. tetragonoloba*, and which plasmids can therefore also be regarded as food-grade.

Figure 4:
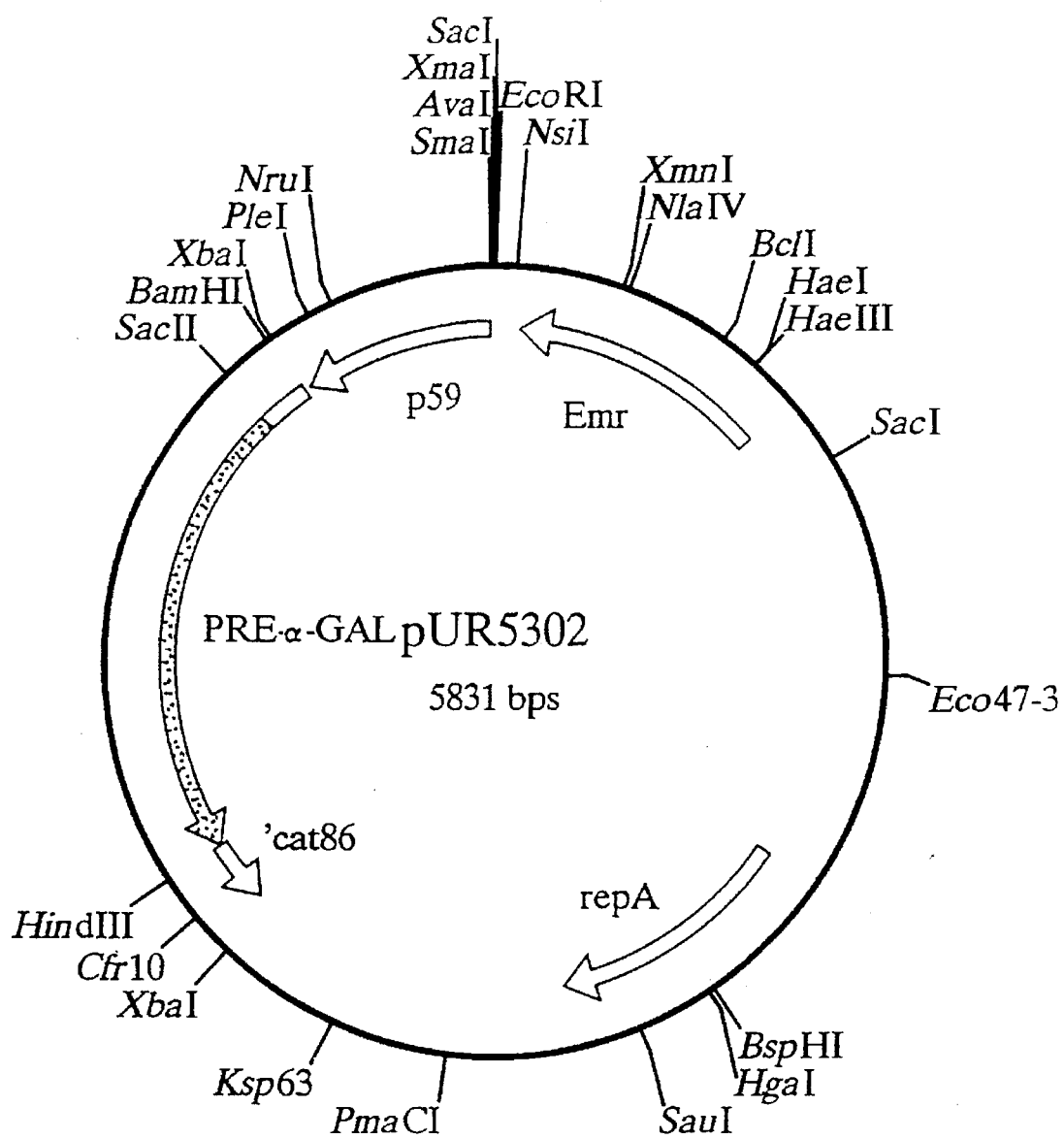
FIG. 4 is a schematic representation of plasmid pUR5302.
Figure 6:
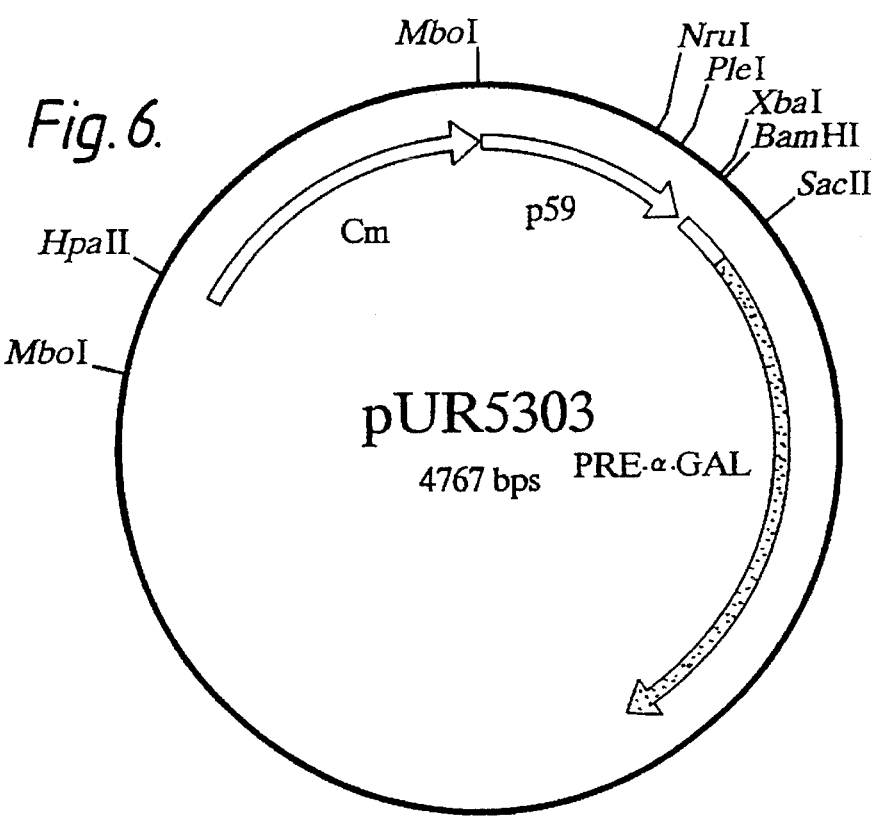
FIG. 6 is a schematic representation of plasmid pUR5303.
Figure 7:
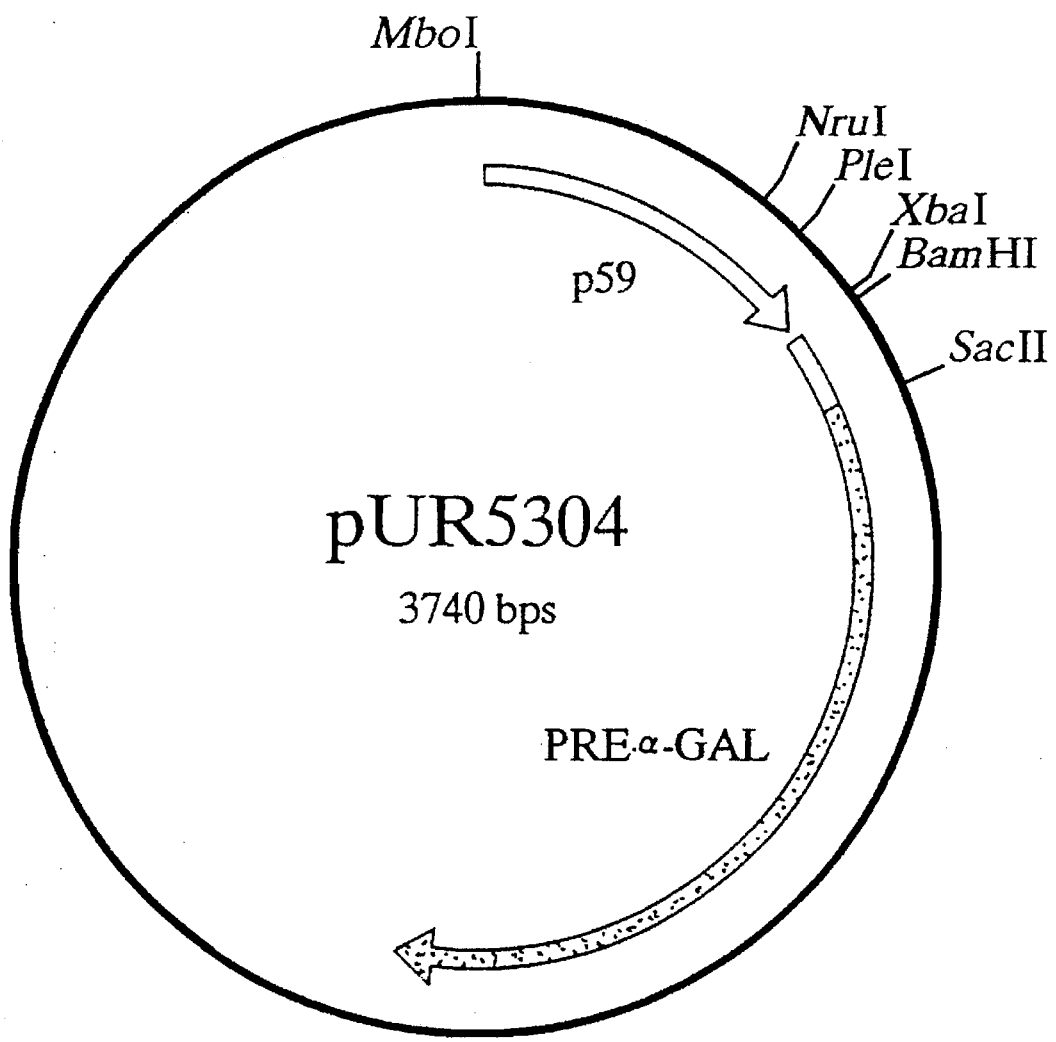
FIG. 7 is a schematic representation of plasmid pUR5304.

The first step is to fuse the mature α-galactosidase gene to a signal sequence isolated from *L. lactis*. Therefore, the BamHI-SacII fragment of pUR5301, containing the *B. amyloliquefaciens* α-amylase signal sequence can be replaced by a (synthetic) BamHI-SacII fragment carrying a signal sequence preceded by a ribosome binding site both derived from *L. lactis* MG1363. From the resulting pUR5302 (FIG. 4) a restriction fragment carrying both the P59 promoter and the pre-α-galactosidase gene, can be cloned in plasmid pGK1 (FIG. 5), a chloramphenicol resistance (Cm$^r$) conferring derivative of the cryptic lactococcal plasmid pWV01 (Kok J., van der Vossen, J., and Venema, G., 1984. Appl. Environ. Microbiol. 48:726–731). Therefore, the SmaI-HindIII fragment from pUR5302 has to be isolated, treated with Klenow enzyme, and cloned in pGK1, from which a ClaI fragment is removed followed by treatment with Klenow of the food-grade vector part, to obtain pUR5303 (FIG. 6). *L. lactis* MG1363 cells transformed with pUR5303 again will be able to produce active α-galactosidase, as can be demonstrated by growth on plates supplemented with X-α-Gal. Finally, plasmid pUR5304 (FIG. 7) can be derived from pUR5303 by deletion of the MboI fragment which carries the Cm$^r$-gene. Since selection on chloramphenicol-containing plates is not possible anymore, the pUR5304 construct can be used to electrotransform cells of the sucrose-fermenting *L. lactis* strain LL-1, which are then grown on plates that contain raffinose or stachyose as sole sugar source. In this way cells will be selected, that as a result of their α-galactosidase activity, are able to release sucrose from raffinose or stachyose, and are therefore able to grow on M17 medium containing said sugars. Moreover, when X-α-Gal is added to the medium the colonies will turn blue.

Example 2

Construction of plasmids containing an inulinase gene and expression in *L. lactis*. The *K. marxianus* inulinase gene is used.

Alternatively, in the plasmids that are mentioned in Example 1, the mature α-galactosidase can be replaced by the mature inulinase gene, isolated from *Kluyveromyces marxianus*. The inulinase enzyme is capable of degrading the polysaccharide inuline exclusively and is also capable of degrading other polysaccharides (like the α-galactosidase enzyme). Selection of the plasmids carrying the inulinase gene, without the use of antibiotics, can be achieved by growth on medium that is supplemented with sugars such as inuline, raffinose or stachyose. When the mature inulinase gene is fused to a lactococcal signal sequence preceded by a strong lactococcal promoter (e.g. P59), *L. lactis* cells containing the plasmids will be able to produce an active inulinase.

Example 3

Construction of plasmids containing the *Lactococcus lactis* subsp. cremoris Wg2 proteinase genes.

Figure 8:
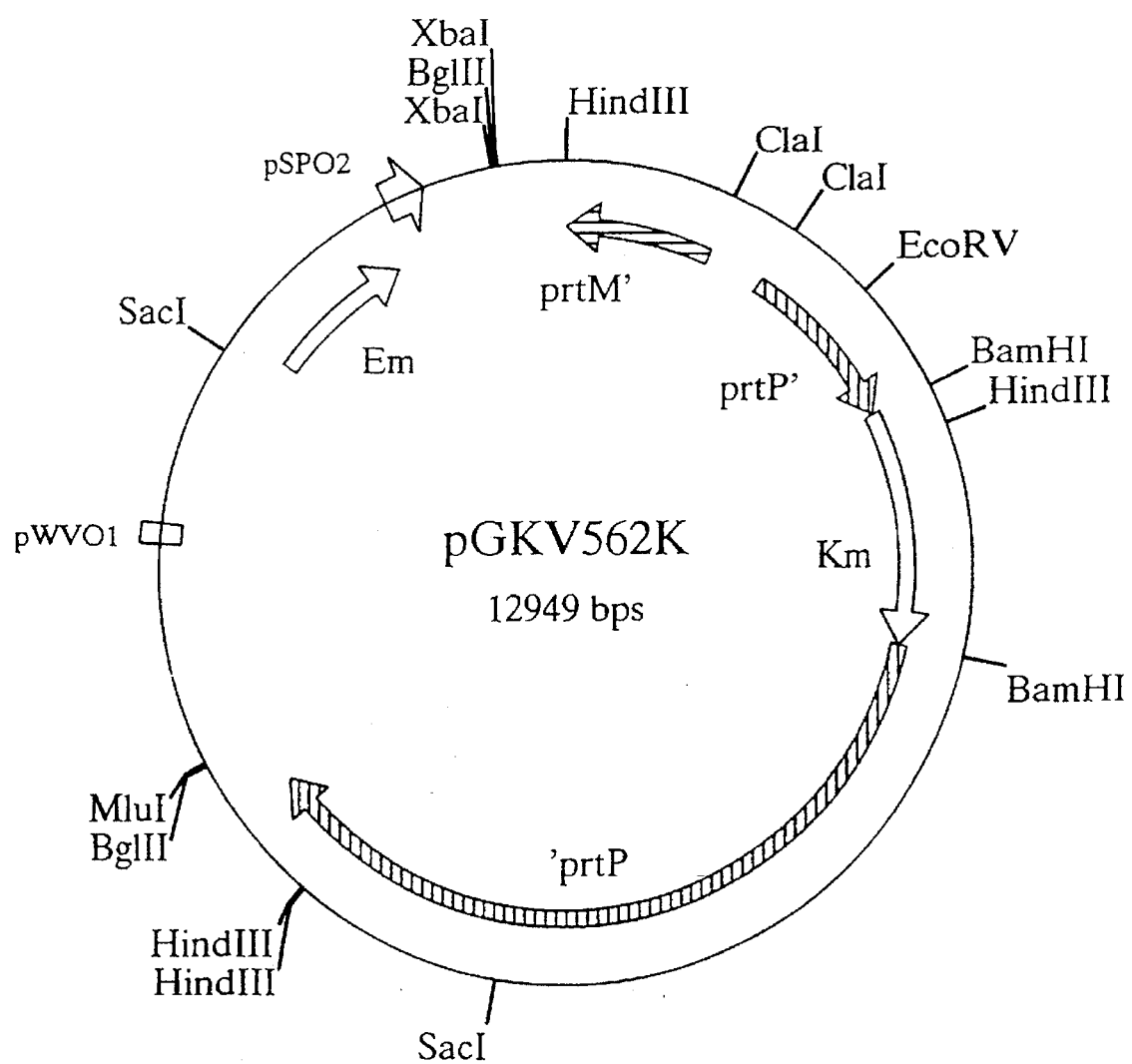
FIG. 8 is a schematic representation of plasmid pGKV562K.

The plasmids pUR5303 and pUR5304 mentioned in Example 1, may also be used for cloning other genes besides the α-galactosidase gene, the latter then serving merely as a (foodgrade) selection marker. In this example the construction of plasmids containing the genes of *Lactococcus lactis* subsp. cremoris Wg2 that are needed for proteinase activity is demonstrated. The presence of both the gene for the cell envelope-associated serine protease (prtP) and the gene encoding a membrane associated lipoprotein (prtM) is essential for proteinase activity (Haandrikman, A. J., Kok, J., Laan, H., Soemitro, S., Ledeboer, A. M., Konings, W. N., and Venema, G., 1989, J.Bacteriol. 171:2989–2999). Plasmid pGKV552 is a derivative of pGKV500 and pGKV550 (Haandrikman, A. J., Kok, J., Laan, H., Soemitro, S., Ledeboer, A. M., Konings, W. N., and Venema, G., 1989, J.Bacteriol. 171:2989–29991 Kok, J., van Dijl, J. M., van der Vossen, J. M. B. M., and Venema, G., 1985, Appl. Environ. Microbiol. 50:94–100) and contains the complete prtP gene and a functional prtM gene from *L. lactis* subsp. cremoris Wg2. A second BglII restriction site was introduced in pGKV552 (the first being located downstream of the prtP gene) as follows: after digestion of the unique XbaI site downstream of prtM, the recessed ends were filled in with Klenow enzyme and the food-grade vector was subsequently ligated to a synthetic 10-mer (5'-AAAGATCTTT-3') (SEQ ID NO:1) BglII linker, resulting in pGKV562. To facilitate easy transfer of the proteinase genes to other plasmids, the unique BamHI restriction site within the coding sequence of the prtP gene was used to insert an 1,4 kb BamHI fragment of pKM1 (Kiel, J. A., Vossen, J. P., and Venema, G., 1987, Mol. Gen. Genet. 207:294–301) carrying the kanamycin resistance (Km$^r$) gene, resulting in pGKV562K (FIG. 8). The 9 kb BglII fragment of pGKV562K carrying the prtM, prtP and Km$^r$ genes can be inserted into the compatible, unique MboI site of pUR5304, resulting in pUR5305. Plasmid pUR5306 with a functional prtP gene is obtained by removing the 1,4 kb BamHI fragment carrying the Km$^r$ gene from the prtP coding sequence in pUR5305. When the resulting pUR5306 is used to electroporate *L. lactis* LL1 cells, transformants can be selected on M17 medium containing raffinose or stachyose, as described above. Furthermore, these transformants will express and secrete a biologically active proteinase, as can be demonstrated by rapid growth in milk, in a stable fashion.

Example 4

Construction of plasmids containing an additional foreign gene, namely for bacteriocin activity and immunity.

Plasmids pUR5303 and pUR5304, as mentioned in the examples 1, 2 and 3, may also be used for cloning of genes for enzymes involved in bacteriocin production and/or immunity. Plasmid pSRQ11 isolated from *Pediococcus acidilactici* PAC1.0 has been shown to encode genes necessary for production of a bacteriocin called pediocin PA-1 (Gonzalez, C. F., and Kunka, B. S. 1987, Appl. Microbiol. 51:105–109). From this plasmid a restriction fragment containing all the required information for bacteriocin activity and/or immunity, can be isolated, and cloned into the MboI site of pUR5304. Selection of transformants containing the resulting constructs is performed similarly to what has been described in the previous example(s).

Example 5

Construction of integration food-grade vectors capable of integration in the *L. lactis* chromosome.

Plasmid pWV01 is a broad-host-range, cryptic plasmid from *L. lactis* that replicates via the rolling circle mode of replication. It encodes the replication initiator protein RepA that can act in trans on the plus origin of pWV01 (Kok, J., van Dijl, J. M., van der Vossen, J. M. B. M., and Venema, G. 1985. Appl. Environ. Microbiol. 50:94–100).

As the first step towards an integration system composed of lactococcal DNA and a food-grade selection marker, a pWV01-based food-grade vector was constructed in which the repA gene is lacking and which is therefore unable to replicate in *L. lactis*. Upon the insertion of a lactococcal chromosomal fragment in this plasmid, stable integration in the L. lactis chromosome was obtained.

Figure 5:
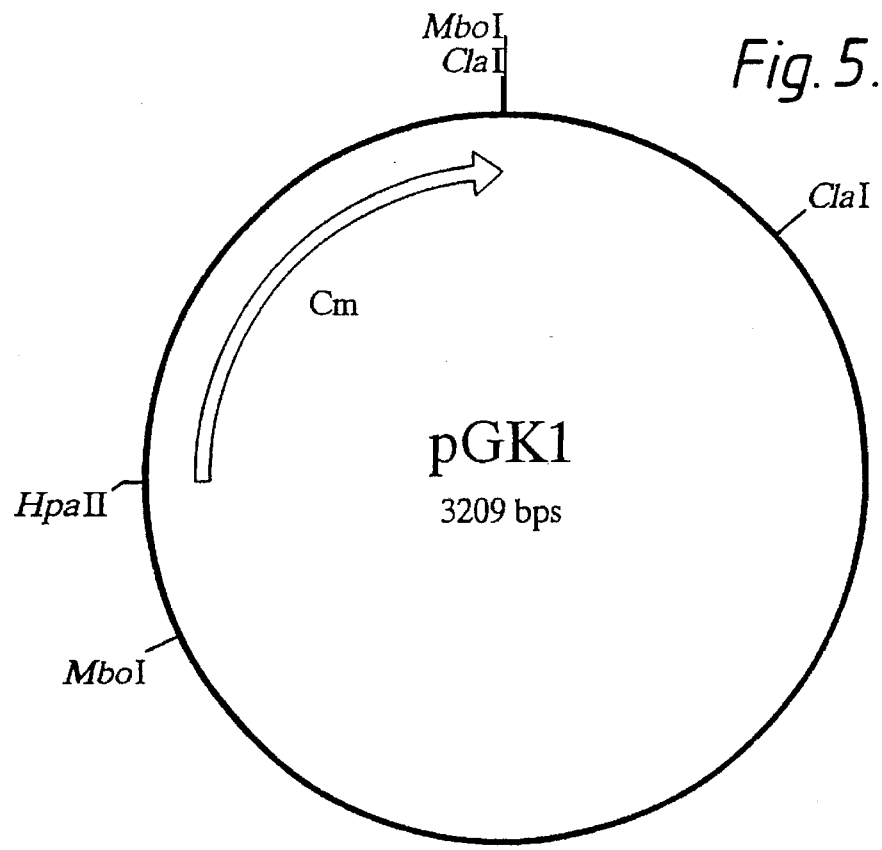
FIG. 5 is a schematic representation of plasmid pGK1.
Figure 9:
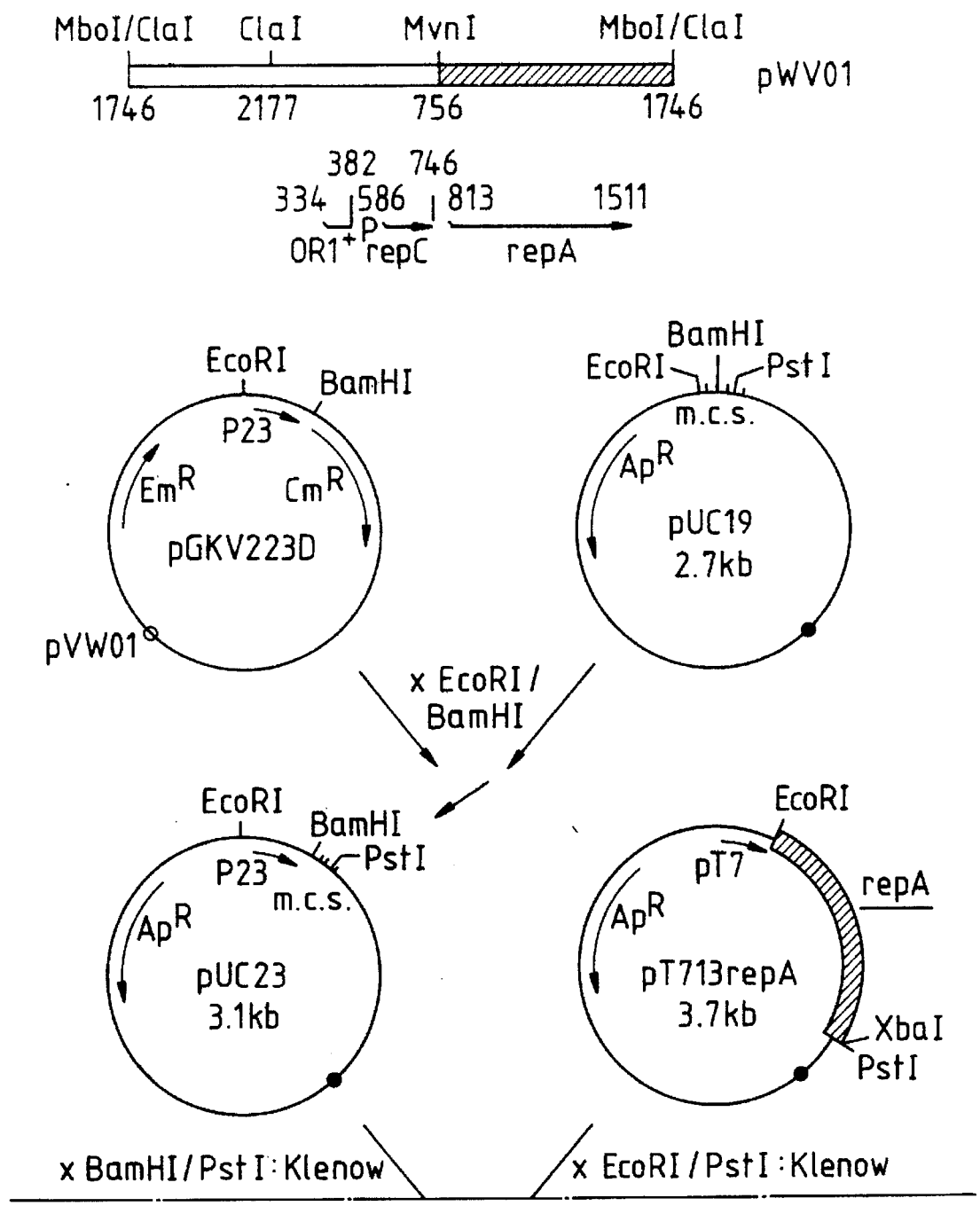
FIG. 9 is a schematic representation of the construction of the B. subtilis integration food-grade vector pREP4.
Figure 9:
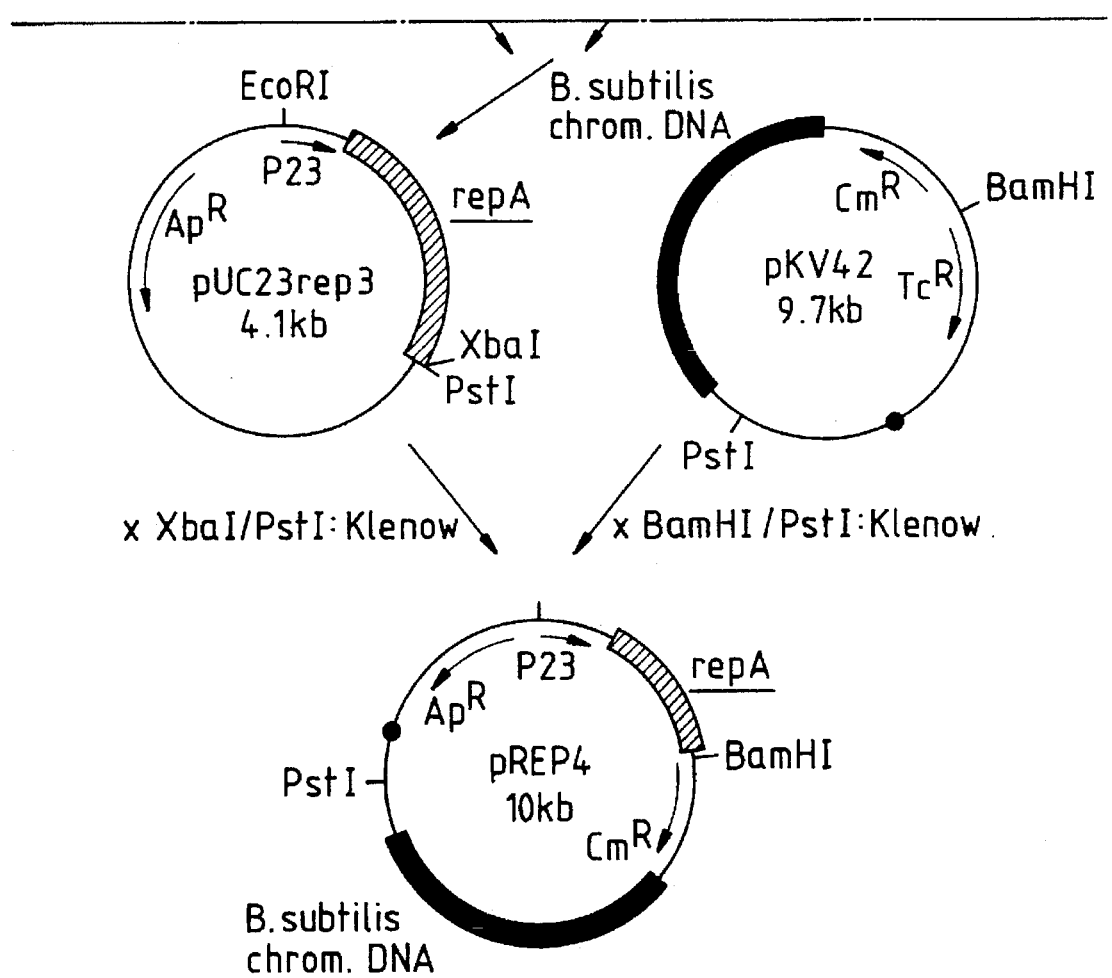
Figure 10:
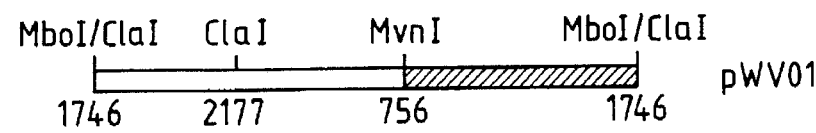
FIG. 10 is a schematic representation of the construction of the L. lactis integration food-grade vector pINT1.
Figure 10:
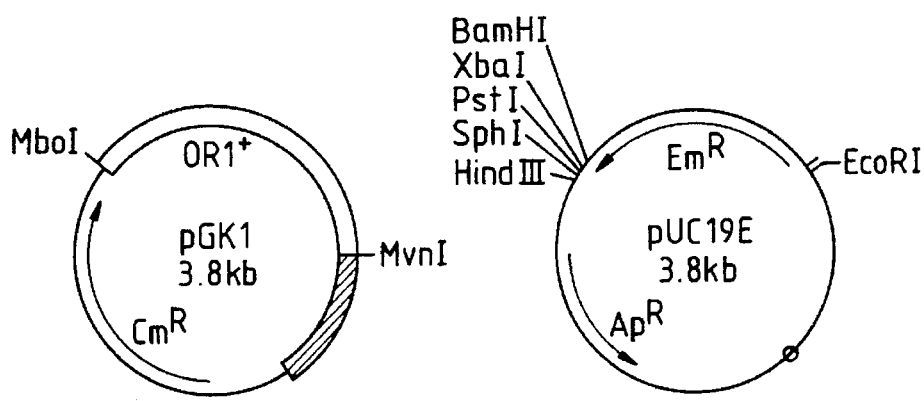
Figure 10:
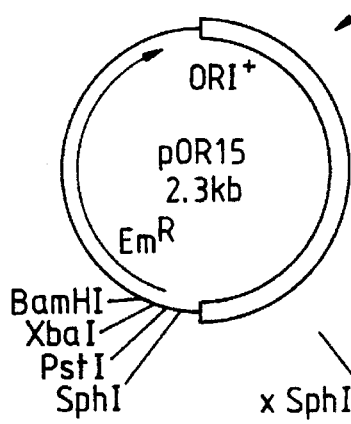
Figure 10:
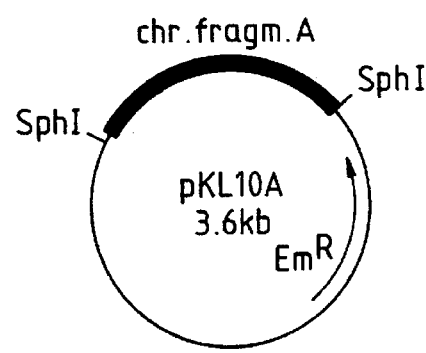
Figure 10:
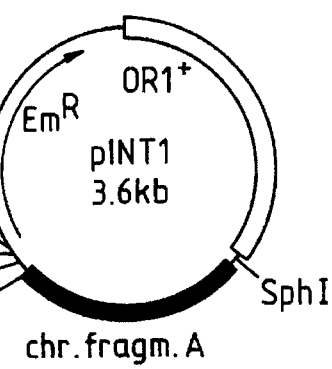

To enable the construction and isolation of this non-replicating integration food-grade vector, first a *B. subtilis* strain was constructed which contained the pWVO1 repA protein gene integrated in its chromosome under the control of the lactococcal promoter P23 (van der Vossen, J. M. B. M., van der Lelie, D, and Venema, G, 1987. Appl. Environ. Microbiol. 53:2452–2457). To that purpose pREP4 carrying the repA gene was constructed (FIG. 9). The 400 bp EcoRI-BamHI fragment carrying the lactococcal promoter P23 from pGKV223d (a deletion derivative of the previously described pGKV223 [van der Vossen, J. M. B. M., van der Lelie, D, and Venema, G, 1987. Appl. Environ. Microbiol. 53:2452–2457]) was ligated into the EcoRI and BamHI restriction sites of plasmid pUC19 (Yanisch-Perron, C., Vieira, J., and Messing, J., 1985. Gene 33:103–119) resulting in the 3.1 kb plasmid pUC23. The repA gene, devoid of its own promoter, but carrying its ribosome binding site, was isolated on EcoRI-PstI fragment from pT713 repA (Leenhouts, K., Tolner, B., Bron, S., Kok, J., Venema, G., and Seegers, J. 1991. Plasmid 26:55–66). The EcoRI recessed ends were filled in using Klenow enzyme and the repA fragment was ligated to Klenow treated pUC23 digested with BamHI and PstI. The resulting 4.1 kb plasmid was designated pUC23rep3. Plasmid pKV42 (Kooistra, J., Vosman, B., and Venema, G., 1988. J. Bacteriol. 170:4791–4797) was the source of chromosomal DNA of *B. subtilis* 8G5. The approximately 6 kb BamHI-PstI fragment carrying the Cm$^r$ gene of pC194 (Horinouchi S., Weisblum, B., 1982. J. Bacteriol. 150:815–825) and the 4.2 kb chromosomal *B. subtilis* DNA was isolated and treated with Klenow enzyme to fill in the BamHI recessed ends. Plasmid pUC23rep3 was digested with XbaI and PstI, treated with Klenow enzyme to fill in the XbaI recessed ends, and ligated to the 6 kb fragment of pKV42 which resulted in pREP4, approximately 10 kb in size. In pREP4 the repA gene is transcriptionally controlled by the lactococcal promoter P23 and this plasmid lacks the pWV01 origin of replication. Plasmid pREP4 was used to transform competent cells of *B. subtilis* 8G5 and transformants were selected on Cm-containing plates. One of the transformants, designated 8G5::repA, carried pREP4 integrated into its chromosome and was used to construct a pWV01-based integration food-grade vector. To construct a plasmid containing the plus origin of replication of pWV01, but lacking the repA gene, use was made of pGK1 (FIGS. 5 and 10). The 1.1 kb MboI-MvnI fragment of pGK1 carrying the plus origin was isolated and treated with Klenow enzyme to fill in the recessed ends. The 1.1 kb EcoRI-HindIII fragment of pUC19E, carrying the Em resistance (Em$^r$) gene of pE194 (Horinouchi, S., Weisblum, B., 1982, J. Bacteriol.

Figure 11:
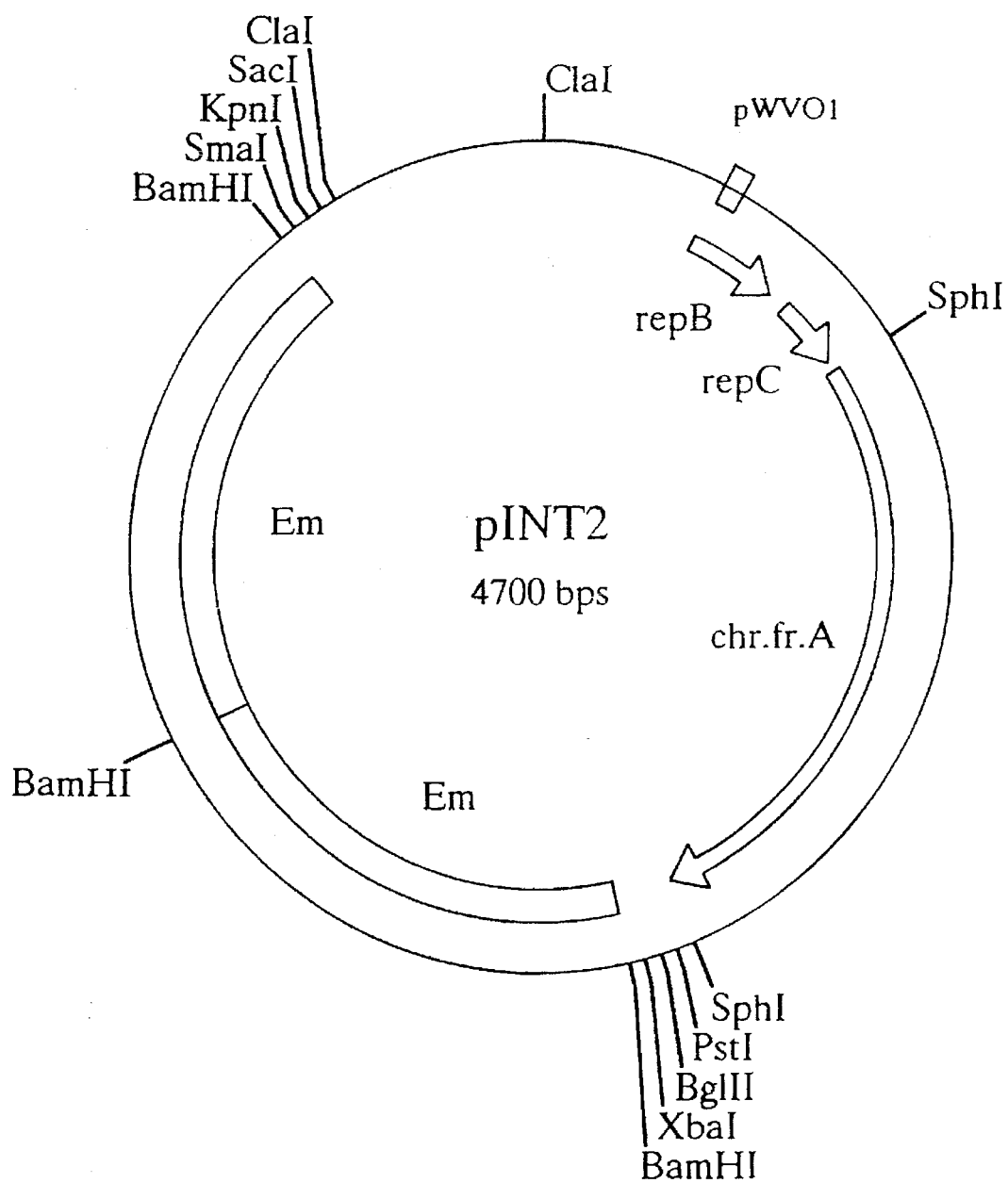
FIG. 11 is a schematic representation of plasmid pINT2.
Figure 12:
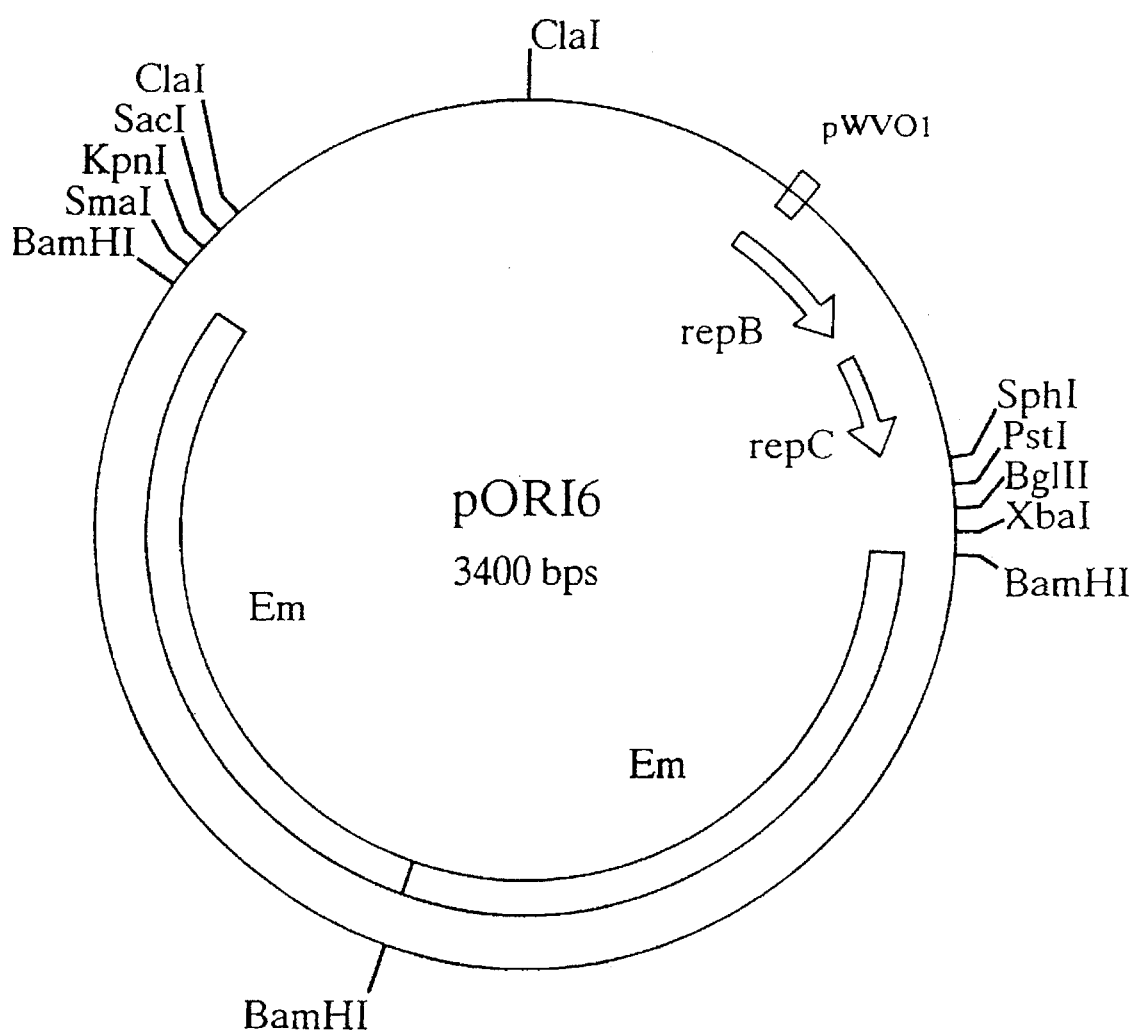
FIG. 12 is a schematic representation of plasmid pORI6.
Figure 13:
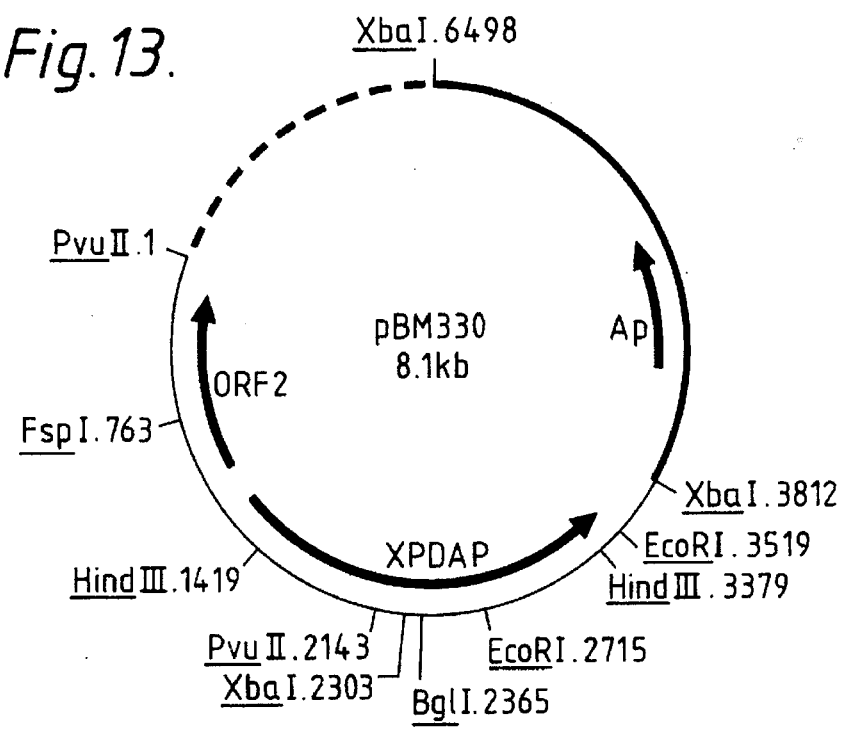
FIG. 13 is a schematic representation of plasmid pBM330.
Figure 14:
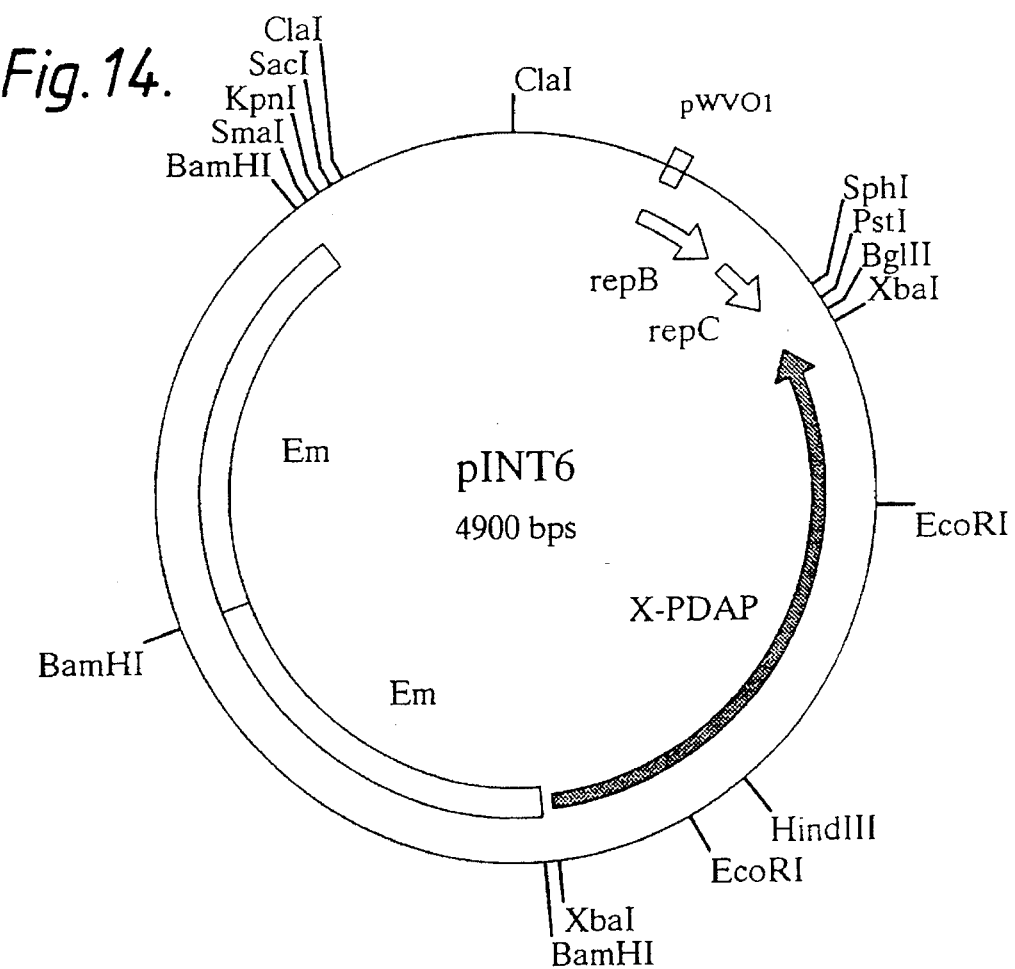
FIG. 14 is a schematic representation of plasmid pINT6
Figure 15:
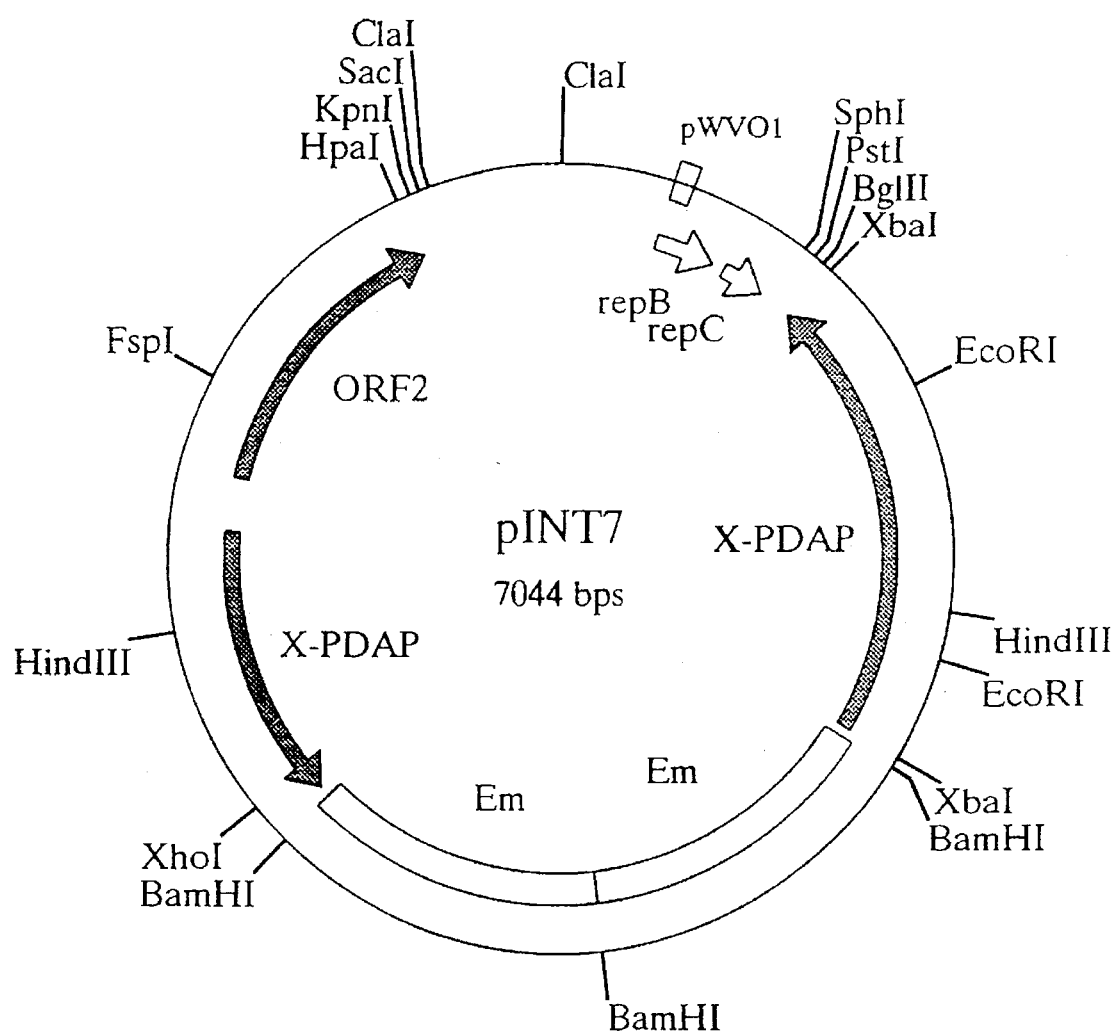
FIG. 15 is a schematic representation of plasmid pINT7

150:804–814), was isolated and treated with Klenow enzyme. *B. subtilis* 8G5::repA protoplasts were transformed with a ligation mixture of the plus origin fragment and the Em$^r$ gene fragment. Transformants which were Cm$^r$ (conferred by the recipient strain) and Em$^r$ (conferred by the plasmid), contained the 2.3 kb plasmid pORI5 which was able to replicate in this strain. In the SphI restriction site of pORI5 the 1.3 kb SphI lactococcal chromosomal fragment A of pKL10A (Leenhouts, K., Kok J., and Venema, G., 1990. Appl. Environ. Microbiol. 56:2726–2735) was inserted resulting in the 3.6 kb integration plasmid pINT1 (FIG. 10). Plasmid pINT2 is a derivative of the latter plasmid which contains additional SmaI, BglII and BamHI sites adjacent to the Em$^r$ gene (FIG. 11). In pINT2 the Em$^r$ gene can easily be removed by digestion with BamHI followed by ligation of the food-grade vector part. *L. lactis* MG1363 was electrotransformed with either pORI5 or pINT1. No Em$^r$ transformants were obtained when pORI5 was used, whereas pINT1 produced approximately 20 transformants per μg plasmid DNA. The transformants did not contain free plasmid DNA, as judged from analysis by standard procedures. Southern analysis, using chromosomal fragment A as a probe, revealed that the transformants contained different numbers of tandemly integrated plasmid copies in their chromosomes. Subsequently, the 1.3 kb chromosomal fragment A of pINT2 was eliminated by digestion with SphI, ligation and transformation to *B. subtilis* 8G5::repA, resulting in pORI6 (FIG. 12). Plasmid pBM330 (FIG. 13), which contains the XPDAP gene (coding for X prolyldiaminopeptidase) of *L. lactis* MG1363 was obtained from Prof. Venema (University of Groningen) and has been described since (Mayo et al. Appl.Env.Microbiol. (1991), 57:38–44). From this plasmid the 1509 bp XbaI fragment has been isolated and ligated into XbaI cut pORI6, giving pINT6 (FIG. 14).

pINT7 can be obtained subsequently by cutting pINT6 with SmaI and ligating the 2143 bp PvuII fragment of pBM330 into this site (FIG. 15). The orientation of the XPDAP gene fragments can be determined by cutting with unique restriction enzymes.

Figure 16:
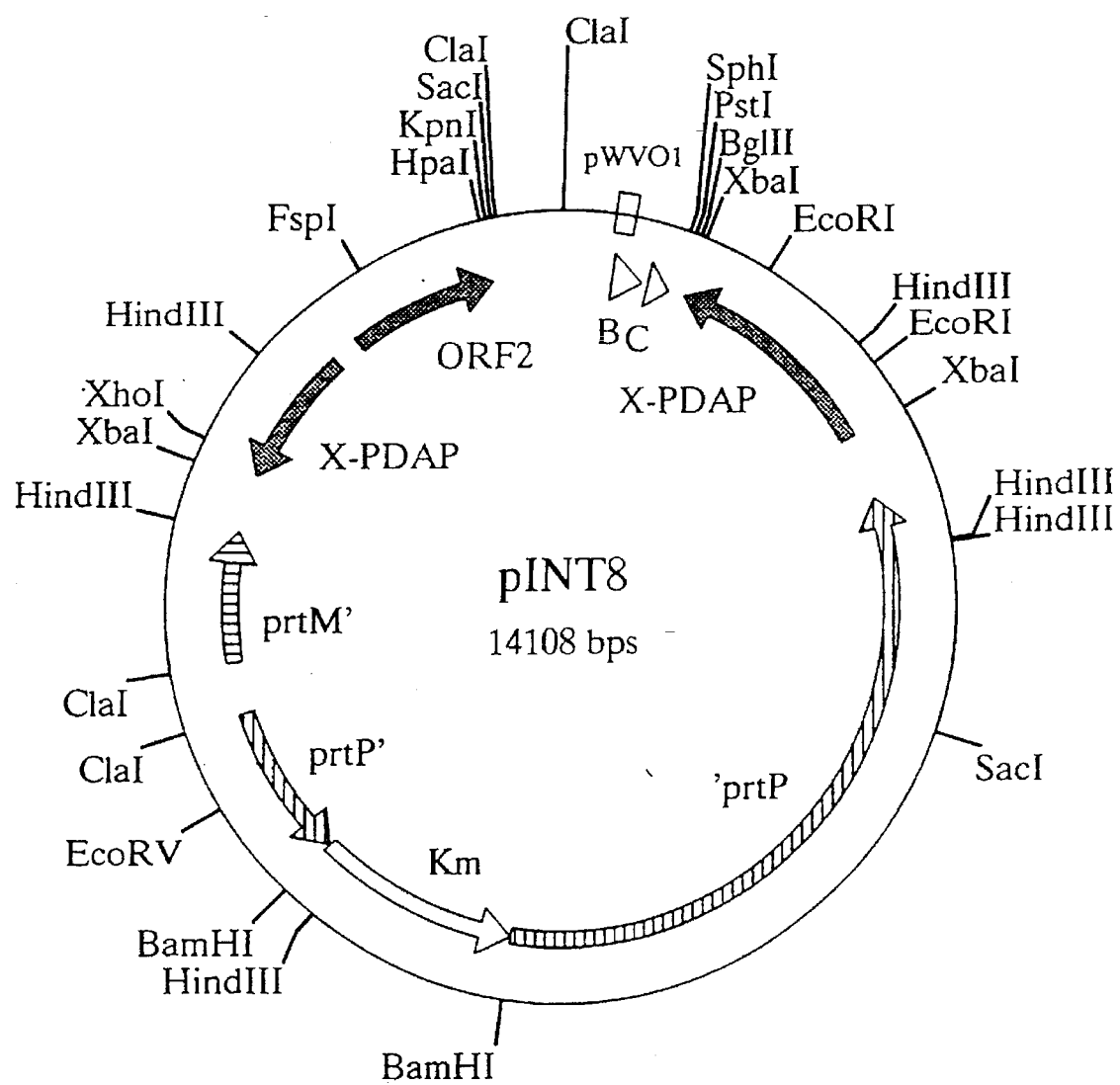
FIG. 16 is a schematic representation of plasmid pINT8

Subsequently, the protease gene of pGKV262K (FIG. 8), inactivated by the insertion of the Km$^r$ gene, can be inserted into pINT7, by ligating the 9 kb BglII fragment into BamHI cut pINT7 and selecting for Km$^r$ transformants in *B. subtilis* 8G5::repA. In the resulting plasmid pINT8, the Em$^r$ gene will be eliminated (FIG. 16).

Figure 17:
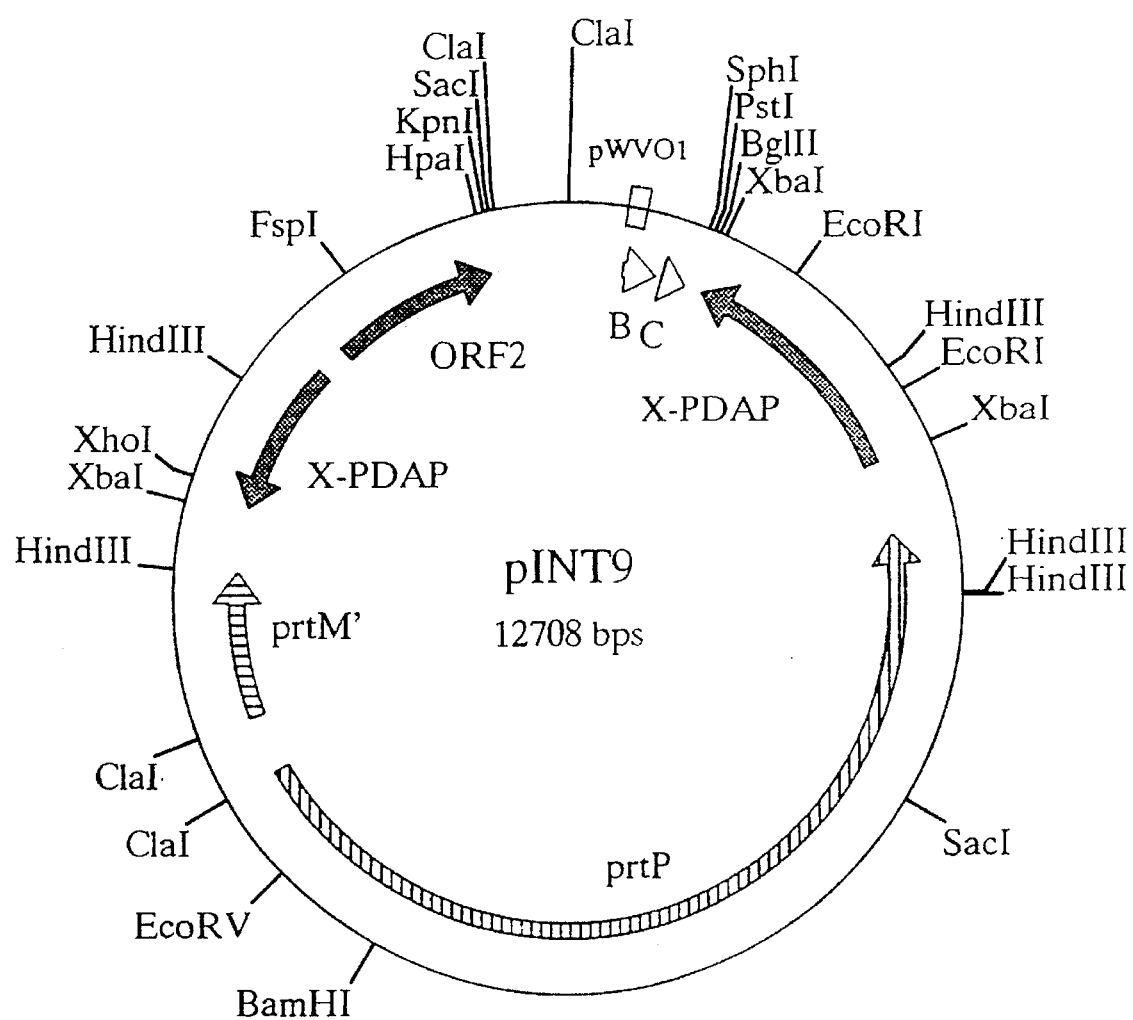
FIG. 17 is a schematic representation of plasmid pINT9

The Km$^r$ gene now can be eliminated by cutting pINT8 with BamHI, ligating it and transforming it to a *L. lactis* strain containing the repA gene, by cotransformation with the selectable non-integrating plasmid pGJS230 (containing an Em resistance marker) (obtained from Prof. Venema, University of Groningen). In this way pINT9 is obtained (FIG. 17).

To integrate pINT9 into *L. lactis* MG1363, the mixture of pINT9 and pGJS230 can be isolated and transformed to a repA$^-$ *L. lactis* MG1363. Em$^r$ transformants are tested for proteolytic activity on GMAB agar plates containing bromocresolpurple. Prt$^+$ strains form yellow colonies and plasmid pGJS230 can be removed by subsequent cultivation of yellow colonies on or in medium that does not contain the antibiotic Em. Two types of integration events can be expected:

Campbell type integrations in which the whole plasmid is integrated by a single cross-over in one or more copies, restoring the disrupted XPDAP gene and resulting in Prt$^+$ XPDAP$^+$ transformants (red colonies on the plate assay as described by Miller et al. J.Bacteriol. 127 (1976) 440–497).

Alternatively, the chromosomal XPDAP gene is disrupted by a double cross-over integration resulting in white XPDAP$^-$ colonies. Selection on XPDAP$^-$ colonies can also be used to integrate any gene of interest into XPDAP producing *L. lactis* strains. Moreover any non-essential selectable gene of a lactic acid bacterium can be used to integrate any gene of interest into said lactic acid bacterium. The protease gene in pINT9 can also be used as a food-grade selection marker. Therefore any gene of interest can be inserted in one of the unique restriction sites of pINT9 not present in the prtP or prtM genes. Examples of such sites are XhoI and BglII. Moreover other unique sites could be introduced.

Example 6

Construction of an integration food-grade vector containing the α-galactosidase gene as selection marker.

From plasmid pUR5302 (see Example 1) the SmaI-HindIII fragment, containing the pre-α-galactosidase gene under the control of the P59 promoter, can be isolated, treated with Klenow enzyme to fill in the HindIII recessed ends, and ligated into the SmaI-digested pINT2. The ligation mixture can be used to transform *B. subtilis* 8G5::repA protoplasts, selecting for transformants, as described above (Example 5). In this way plasmid pINT3 can be obtained. By removing the Em$^r$ gene via deletion of a BamHI fragment from pINT3, plasmid pINT4 can be obtained. Selection for transformants containing pINT4 is achieved by making use of a derivative of the sucrose fermenting *L. lactis* strain LL-1, designated LL-l::repA, which carries the pWV01 repA gene integrated in the chromosome. This strain is obtained by transformation of LL-1 with a pREP4-derivate in which the chromosomal *B. subtilis* DNA fragment is replaced by a chromosomal *L. lactis* DNA fragment. When pINT4 is used to electrotransform a sucrose fermenting *L. lactis* strain which does not contain the repA gene, selection for α-galactosidase activity on M17 medium supplemented with raffinose or stachyose, will result in stable integration of the plasmid into the chromosome of the host.

Example 7

Construction of an integration vector containing the sucrose genes as a selection marker.

Figure 18:
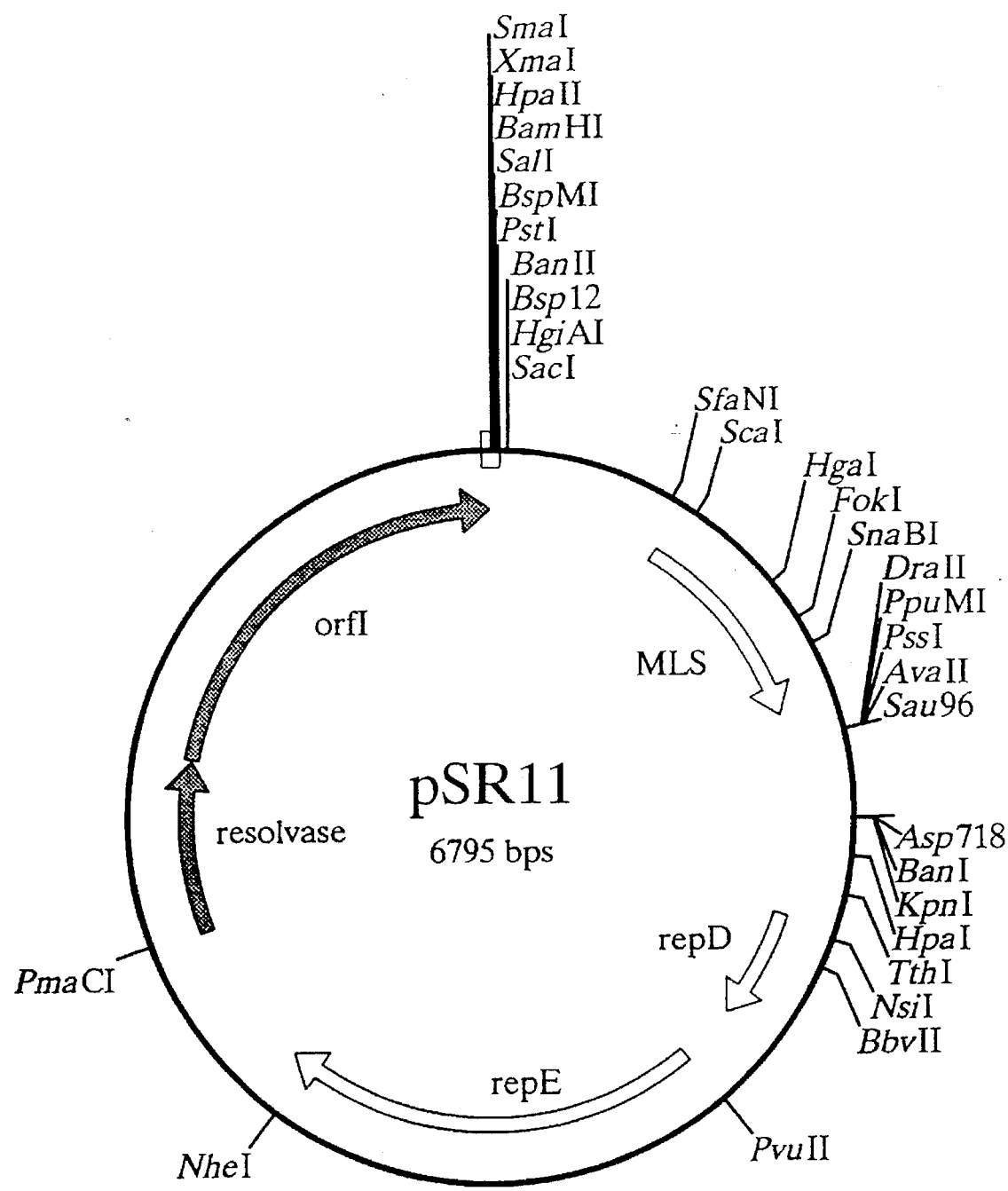
FIG. 18 is a schematic representation of plasmid pSRll

Plasmid pSRQ1 isolated from *Pediococcus pentosaceus* PPE1.O has been shown to encode genes necessary for growth on sucrose (Gonzalez, G. F., and B. S. Kunka, 1986. Appl. Environ. Microbiol. 51:105–109). This plasmid was digested with BamHI and the restriction fragments were cloned into the BamHI site of psR11 (FIG. 18). Selection of transformants was on M17 plates that contained sucrose, erythromycin and the pH indicator bromocresolpurple. All transformants which showed growth on these plates and acidification of the medium (yellow color), contained plasmid pSR12. This plasmid carried a 15.5-kb BamHI insert in pSRll. Said insert containing all the genes necessary for growth on sucrose was isolated as a BamHI fragment and ligated to the vector part of pINT2 (FIG. 11), from which the Em$^r$ gene was removed by digestion with BamHI (as described in example 5). In this way plasmid pINT100 was obtained, which is approximately 18 kb in size. Selection for transformants containing pINT100 was achieved by making use of a derivative of the sucrose negative (suc$^-$) *L. lactis* strain MG1363, designated LL108, which carries the pWV01 repA gene integrated in the chromosome. This strain was obtained by transformation of MG1363 with a pREP4-derivative in which the chromosomal *B. subtilis*

DNA was replaced by the chromosomal L. lactis DNA fragment A. When pINT100 was used to electrotransform the suc⁻ L. lactis strain MG1363 which does not contain the repA gene, selection for suc⁺ transformants on M17 medium containing sucrose, resulted in stable integration of the plasmid into the chromosome of the host.

Figure 19:
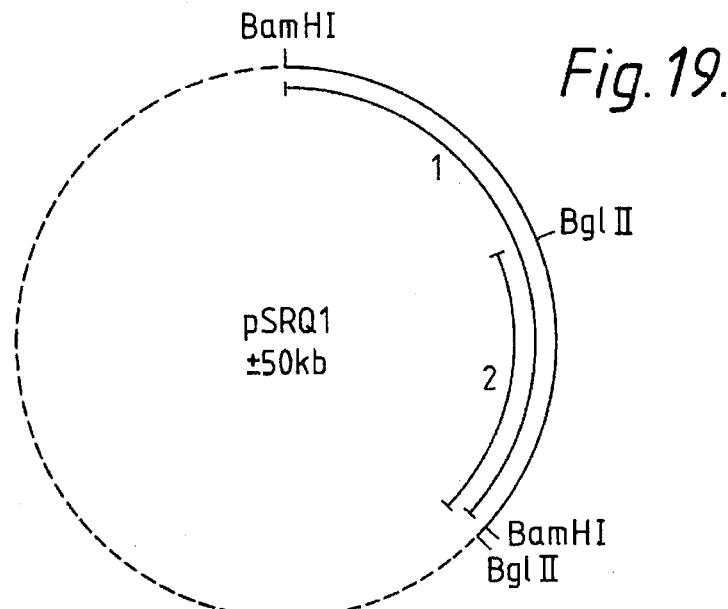
FIG. 19 is a schematic representation of plasmid pSRQ1
Figure 20:
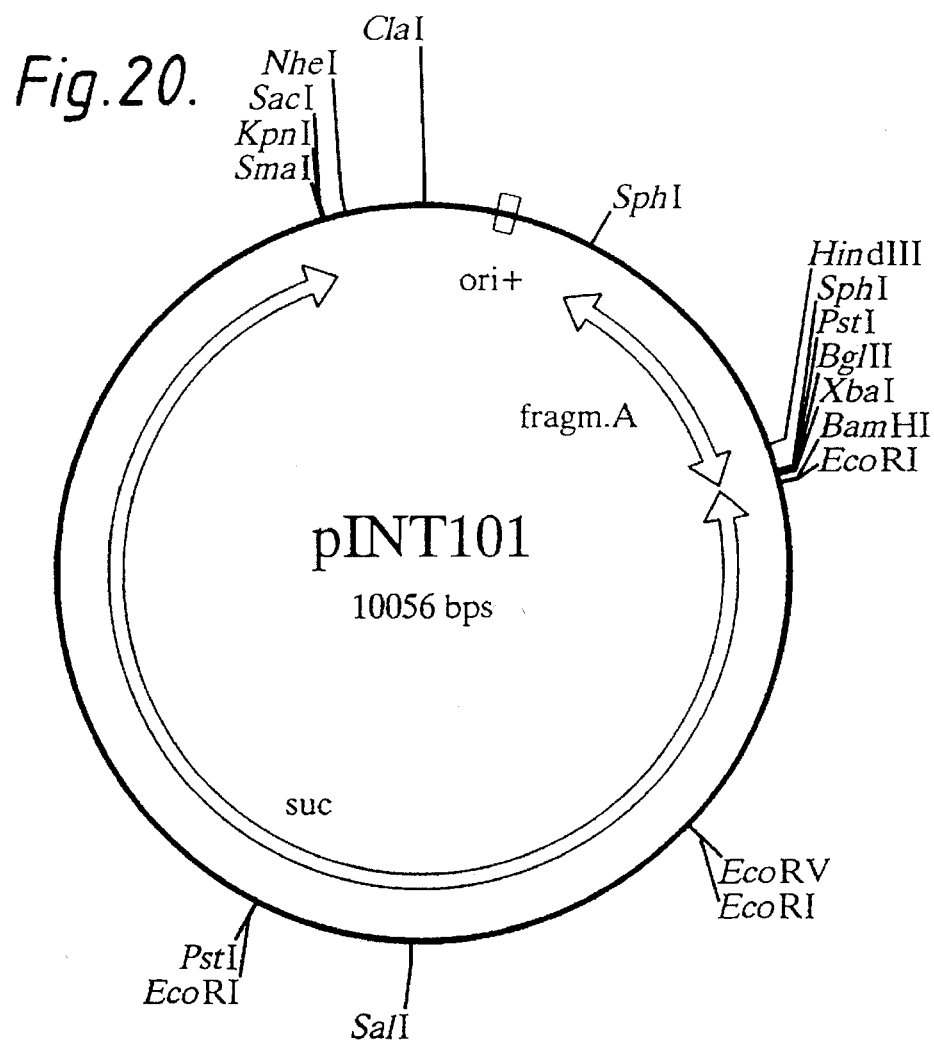
FIG. 20 is a schematic representation of plasmid pINT101.

A smaller construct was made by digestion of pSRQ1 with BglII and cloning of these fragments into the BamHI vector part of pINT2. Selection for transformants was as described above, using the RepA⁺ L. lactis strain LL108. All suc⁺ transformants contained in the pINT vector a 7.5-kb insert, which largely overlaps the 15.5-kb BamHI fragment (FIG. 19). This plasmid, approximately 10 kb in size was designated pINT101 (FIG. 20). Said plasmid was stably integrated into the RepA⁻ L. lactis strain MG1363 by electro-transformation of this strain and by selection as described above.

We claim:

1. A food-grade vector suitable for transforming a food-grade host cell, said vector comprising:
   1) a nucleic acid which hybridizes with a non-essential portion of chromosomal DNA of a non-transformed host cell enabling said vector to integrate stably into a chromosome of said host cell after transformation to form a transformed host cell without leading to a loss of an essential function of said host cell, wherein said host cell is a lactic acid bacterium; and
   2) foreign DNA selected from the group consisting of
      i. foreign DNA having a DNA sequence that codes for a food-grade selectable marker enabling the transformed host cell to metabolize a substrate that cannot be metabolized by the non-transformed host cell, where at least said DNA sequence and the product encoded by said DNA sequence are foreign for a prototrophic strain of said non-transformed host cell,
      ii. foreign DNA having a DNA sequence that codes for at least one product enabling the transformed host cell to grow in the presence of a food-grade natural bacteriocidal agent wherein at least said DNA sequence and the product encoded by said sequence are foreign for the non-transformed host cell, and
      iii. a mixture of both (i) and (ii);
the food-grade vector being suitable for transforming a food-grade gram positive bacterial host cell, and the food-grade vector having been made incapable of autonomously replicating in the bacterial host cell by removal of its replicase gene.

2. A food-grade vector according to claim 1, wherein the foreign DNA comprises a DNA sequence from Lactococcus lactis.

3. A food-grade vector according to claim 1, wherein one of the stretches of nucleotides that enables integration is from chromosomal DNA that is present in multiple copies in the non-transformed host cell.

4. A food-grade vector according to claim 1, wherein the nucleic acid that enables integration is from DNA that comprises at least part of a non-essential portion of the chromosome of the non-transformed host cell.

5. A food-grade vector according to claim 1, wherein the nucleic acid that enables integration is from DNA that comprises at least part of a marker gene of the chromosome of the non-transformed host cell.

6. A food-grade vector according to claim 1, wherein foreign DNA comprising a DNA sequence coding for a product enabling the transformed host cell to metabolize a substrate that is not metabolizable in the non-transformed host cell is situated between two non-identical nucleic acids that enable integration.

7. A food-grade vector according to claim 1, wherein foreign DNA comprising a DNA sequence coding for a product enabling the transformed host cell to grow in the presence of a foodgrade natural bacteriocidal agent non-transformed is situated between two non-identical nucleic acids that enable integration.

8. A food-grade vector according to claim 1, wherein a stretch of nucleotides that enables integration is from chromosomal DNA encoding xprolyldiaminopeptidase (XPDAP).

9. A food-grade vector according to claim 1, wherein said foreign DNA sequence encodes an enzyme involved in the biosynthesis of essential amino acids.

10. A food-grade vector according to claim 1, wherein said foreign DNA sequence encodes a proteolytic enzyme.

11. A food-grade vector according to claim 1, wherein said foreign DNA sequence encodes an enzyme involved in the biosynthesis of a food flavour or colour compound.

12. A food-grade vector according to claim 1, wherein said vector is derived from the Lactococcus plasmid pWV01.

13. A process for producing a transformed food-grade host cell, wherein a food-grade vector according to claim 1 is used for transforming the host cell and subsequently stably integrating foreign DNA in the chromosomal DNA of said transformed host cell.

14. A process for producing a transformed food-grade lactic acid bacterium, wherein a food-grade vector according to claim 1 is used for cotransforming the lactic acid bacterium and subsequently stably integrating foreign DNA in the chromosomal DNA of said transformed lactic acid bacterium, said cotransformation occurring with a selectable plasmid, said plasmid subsequently being lost from the cotransformed lactic acid bacterium after removal of the selective pressure used for maintaining said plasmid in the transformed lactic acid bacterium.

15. A process according to claim 13, wherein a host cell containing said stably integrated vector can be selected due to the ability of said host cell to metabolize a substrate that the non-transformed host cell cannot metabolize.

16. A process according to claim 13, wherein a hot cell containing said stably integrated vector can be selected due to the ability of said host cell to grow in the presence of a food-grade natural bacteriocidal agent in contrast to the non transformed host cell.

17. A process according to claim 13, wherein a host cell containing said stably integrated vector can be identified by elimination of the activity of the gene in which said vector is integrated.

18. A host cell containing a food-grade vector according to claim 1 that is stably integrated into the chromosome of said host cell.

19. A host cell produced through a process according to claim 13.

20. A host cell according to claim 18, wherein said host cell is a lactic acid bacterium selected from the group consisting of food-grade strains of the genera Bifidobactedum, Enterococcus, Lactobacillus, Lactococcus, Leuconostoc, Pediococcus, Streptococcus, Propionibacterium and Staphylococcus.

21. A process for biosynthesis of essential amino acids, food flavor or color compounds wherein either the intact cells according to claim 18 or their homogenates or purified forms of homogenates are used to metabolize a food-grade substrate.

22. A fermentation process, wherein a host cell according to claim 18 is used to fermet a food-grade substrate.

23. A food-grade vector according to claim 1, wherein the food-grade selectable marker is a proteinase.

24. A food-grade vector according to claim 1, wherein said vector comprises foreign DNA coding for a proteinase and a further DNA sequence coding for a maturase.

25. A food-grade vector according to claim 1, wherein the selectable marker encodes α-galactosidase, inulinase or sucrose hydrolase.

26. A food-grade vector according to claim 25, wherein the selectable marker encodes a functional α-galactosidase obtained from a source selected from the group consisting of a guar gum, a yeast *Saccharomyces carlsbergensis*, a plant *Cyamopsis tetragonoloba*, a plant *Verbascum thapsus*, and a lactic acid bacterium.

27. A food-grade vector according to claim 26, wherein the lactic acid bacterium is *Pediococcus pentosaceus*.

28. A food-grade vector according to claim 25, wherein the selectable marker encodes a functional inulinase from yeast *Kluyveromyces marxianus* or a yeast *Aspergillus niger*.

29. A food-grade vector according to claim 25, wherein the selectable marker encodes a functional sucrose hydrolase from lactic acid bacterium *Pediococcus pentosaceus*.

30. A food-grade vector according to claim 1, wherein said foreign DNA further comprises DNA encoding a signal sequence of an enzyme of the non-transformed host cell.

* * * * *